(12) United States Patent  
Harran et al.

(10) Patent No.: US 7,517,895 B2
(45) Date of Patent: *Apr. 14, 2009

(54) SYNTHETIC DIAZONAMIDES

(75) Inventors: Patrick G. Harran, Dallas, TX (US); Jing Li, Dallas, TX (US); Susan Jeong, Dallas, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 366 days.

This patent is subject to a terminal disclaimer.

(21) Appl. No.: 11/264,502

(22) Filed: Oct. 31, 2005

(65) Prior Publication Data

US 2006/0089397 A1    Apr. 27, 2006

Related U.S. Application Data

(63) Continuation-in-part of application No. 10/227,509, filed on Aug. 23, 2002, now Pat. No. 7,022,720.

(60) Provisional application No. 60/314,674, filed on Aug. 24, 2001.

(51) Int. Cl.
  A61P 35/00    (2006.01)
  A61K 31/425   (2006.01)
  C07D 291/00   (2006.01)
(52) U.S. Cl. .................. 514/366; 514/375; 540/457
(58) Field of Classification Search ................ 514/366, 514/375; 540/457
See application file for complete search history.

(56) References Cited

U.S. PATENT DOCUMENTS 7,022,720 B2 * 4/2006 Harran et al. ............... 514/366

OTHER PUBLICATIONS

Bagley et al., Tetrahedron Lett. (2000) 41:6897-6900.
Bagley et al., Tetrahedron Lett. (2000) 41:6901-6904.
Belshaw et al., Science (1999) 284:486-489.
Belshaw et al., Chem. Biol. (1998) 5:373-384.
Boto et al., Tetrahedron Lett. (1998) 39:8167-8170.
Chan et al., Tetrahedron Lett. (2000) 41:835-838.
Cragg, J. Nat. Prod. (1997) 60:52-60.
Fuerst et al., Org. Lett. (2000) 2:3521-3523.
Gelfand and Bershadsky, Ann. Rev. Cell Biol. (1991) 7:93-116.
Hang et al., Synthesis (1999) 398-400.
Jeong et al., J. Org. Chem. (1998) 63:8640-8641.
Kreisberg et al., Tetrahedron Lett. (2001) 42:627-629.
Lach et al., Tetrahedron Lett. (2000) 41:6893-6896.
Li et al., Angew Chem. Int. Ed. (2001) 40:2683-2685.
Li et al., Angew Chem. Int. Ed. (2001) 40:4765-4769.
Li et al., Angew Chem. Int. Ed. (2001) 40:4770-4773.
Lindquist and Fenical, J. Am. Chem. Soc. (1991) 113:2303-2304.
Lindquist, Ph.D. thesis (1989) University of California at San Diego.
Magnus et al., Tetrahedron Lett. (2000) 41:831-834.
Magnus et al., Tetrahedron Lett. (1999) 40:451-454.
Moody et al., J. Chem. Soc. Perkin Trans. (1996) 16:2413-2419.
Moody et al., Pure Appl. Chem. (1994) 66:2107-2110.
Negishi et al., Tetrahedron Lett. (1986) 27:2829.
Nicolaou et al., Angew Chem. Int. Ed. (2001) 40:4705-4709.
Nicolaou et al., Angew Chem. (2001) 113:4841-4845.
Nicolaou et al., Angew Chem. Int. Ed. (2000) 39:3473-3478.
Nicolaou et al., Angew Chem. (2000) 112:3615-3620.
Ritter and Carreira, Angew Chem. Int. Ed. (2002) 41:2489-2495.
Shu, J. Nat. Prod. (1998) 61:1053-1071.
Takahashi et al., J. Am. Chem. Soc. (1995) 117:11039-11040.
Vedejs et al., Org. Lett. (2001) 3:2451-2454.
Vedejs et al., Org. Lett. (2000) 2:1031-1032.
Vedejs et al., Org. Lett. (2000) 2:1033-1035.
Vervoort, Ph.D. thesis (1999) "Novel anticancer agents from Ascidiacea," University of California, San Diego, Scripps Institution of Oceanography.
Wilson, Chemical and Engineering (2001) 79:11.
Wipf et al., Org. Lett. (2001) 3:1261-1264.
Wipf et al., Tetrahedron Lett. (1998) 39:2223-2226.

* cited by examiner

*Primary Examiner*—Brenda L Coleman
(74) *Attorney, Agent, or Firm*—Morrison & Foerster LLP

(57) ABSTRACT

The application discloses novel synthetic compounds, modeled after unique toxins extracted from the marine invertebrate *Diazona angulata* useful in the treatment abnormal cell mitosis. The application also discloses novel methods for synthesis of these compounds and methods of using these compounds.

10 Claims, 14 Drawing Sheets

30

(−)-diazonamide A (revised Structure)

31

(−)-diazonamide B (revised Structure)

SYNTHETIC DIAZONAMIDES

CROSS-REFERENCE TO RELATED APPLICATIONS

This Application is a continuation-in-part of U.S. patent application Ser. No. 10/277,509, filed Aug. 23, 2002 (now, U.S. Pat. No.), and further claims priority to U.S. Provisional Application Ser. No. 60/314,674, filed Aug. 24, 2001, which is incorporated herein by reference in its entirety.

STATEMENT OF RIGHTS TO INVENTIONS MADE UNDER FEDERALLY SPONSORED RESEARCH

This invention was made with grant support from NIH (RO1-GM6059103) and NSF (CHE-9984282). Thus, the government has certain rights in this invention.

BACKGROUND OF INVENTION

The present invention relates to peptide chemistry. More particularly, it relates to the synthesis of anti-mitotic compounds that have use as anti-proliferative and anti-cancer agents. The compounds, which are synthetic peptide derivatives, are similar to natural substances, called diazonamides and analogues, originally isolated from a marine invertebrate, *Diazona angulata*. This invention relates to anti-mitotic diazonamides and analogues thereof, their use as anti-proliferative and anti-cancer agents, and methods of synthesis.

Cell mitosis is a multi-step process that includes cell division and replication. It is characterized by the intracellular movement and segregation of organelles, including mitotic spindles and chromosomes. Organelle movement and segregation are facilitated by tubulin polymerization. Microtubules are polymers of globular tubulin subunits formed into cylindrical tube structures. The dynamic polymerization of these structures is essential for cell mitosis. Gelfand and Bershadsky, "Microtubule dynamics: mechanism, regulation and function," Ann Rev Cell Biol 1991 7:93-116.

Antimitotic compounds such as colchicine, vinblastine and taxol can inhibit microtubule polymerization. These compounds restrict tubulin polymerization and cells treated with these compounds become arrested in mitosis. During mitosis, tubulin subunits of the mitotic spindle are exchanged in a continual process with the pool of cellular tubulin. Taxol, for example, is a microtubule stabilizing drug that prevents depolymerization of the microtubules. Since blockage of spindle formation preferentially inhibits rapidly dividing cells, microtubule inhibitors have been effective agents against disorders which exhibit abnormal cell mitosis, such as cancer.

The products of secondary metabolic pathways in plants and microorganisms are a proven resource for structurally diverse and functionally unique small molecules which bind, covalently modify, or otherwise alter the function of proteins. Natural product ligands for human and pathogen proteins have revolutionized medicine in this century and have become both models and inspiration for the drug development enterprise. Cragg, J Nat Prod, 1997, 60:52-60; Shu, J Nat Prod, 1998, 61:1053-1071; Nicolaou et al. Angew Chem Int Ed, 2000, 39:44. A number of biological metabolites isolated from various sources, such as sponges, marine organisms and bacteria have been found to possess, in particular, anti-cancer activity. Fenical, "New pharmaceuticals from marine organisms," Trends Biotech 1997, 15:339-341.

In 1991, Fenical and Clardy reported the composition and skeletal stereochemistry of two unique toxins extracted from tissues of the marine invertebrate *Diazona angulata*. Lindquist et al. J Am Chem Soc, 1991, 113:2303-2304. The structure of the major isolate, termed diazonamide B (1a, FIG. 1), was revealed upon X-ray diffraction measurements on a crystal of a p-bromobenzamide derivative (2, FIG. 1). These two new compounds represented a new class of halogenated, highly unsaturated cyclic peptides containing derivatives of three common amino acids, tyrosine (C1-C9), tryptophan (C18-C27) and valine (C31-35). (see 1 and 2, FIG. 1). These molecules possess an unusually rigid skeleton with little conformational freedom for the polycyclic core.

The diazonamides are a particularly complex expression of the more common polyoxazole/thiazole motif observed in peptidyl metabolites isolated from the marine environment. Belshaw et al. Science 1999, 284:486-489; Belshaw et al. Chem Biol, 1998, 5:373-84. Diazonamides comprise a complex arrangement of aromatic or heteroaromatic rings linked together as biaryls or as an intermediate quaternary center. Their synthesis requires three basic peptide modifications, 1) oxidative intramolecular coupling of aromatic side chains (forming cyclic biaryls and biaryl ethers), 2) electrophilic aromatic substitution, and 3) dehydrative cyclization to form oxazole and thiazole rings. An aromatic segment of unknown origin (C10-C17) and four proteinogenic amino acids have been incorporated into a rigid heterocyclic network which permits little extended conjugation of electron density. The fully substituted bis-oxazole (C26-C3 1), the C16-C18 biaryl linkage, and the hindered C10 quaternary center present a challenging molecule for synthesis.

In addition, diazonamide A has demonstrated potent anti-neoplastic activity. Lindquist et al. J Am Chem Soc, 1991, 113:2303-2304. In HCT-116 cells, a human colorectal carcinoma line, diazonamide exhibits $GI_{50}$ values (50% growth inhibitory concentration) of less than 15 ng/ml.

Naturally occurring diazonamide A sent for differential cytotoxicity analysis in the NCI 60 cell mean graph screening profile (COMPARE analysis) identified a correlation with known anti-mitotic agents, such as vinblastine, paclitaxel (taxol) and vincristine. (See Table 1 below.) Hélène C. Vervoort, PhD thesis, 1999, "Novel anticancer agents from Ascidiacea," University of California, San Diego (Scripps Institution of Oceanography). The NCI (National Cancer Institute) 60-cell line human tumor screen is a measure of the effectiveness of a compound for inhibiting or killing various human cancers. It is a set of 60 different cancer cell lines against which chemical compounds can be tested against to determine if the compound has anti-cancer activity. Each compound has an individual "fingerprint" based on effectiveness in killing each of the 60 cancer cell lines. The 50% growth inhibitory concentration (GI50), total growth inhibitory concentration (TGI), 50% lethal concentration (LC50) for any single cell line are indexes of cytotoxicity or cytostasis. A pairwise correlation coefficient (PCC) is calculated for each compound in the database. Those compounds with the highest correlation coefficient are most similar to diazonamides. As a result, these compounds represent a new class of anti-tumor agents.

TABLE 1

COMPARE Analysis - Diazonamide in comparison to known anti-mitotic compounds.

| Compound | GI50 (PCC) | Compound | TGI (PCC) | Compound | LC50 (PCC) |
|---|---|---|---|---|---|
| Vinblastine (antimitotic) | 0.696 | Vinblastine (antimitotic) | 0.679 | Mitindomide (Topo. II Inhibitor) | 0.992 |
| Maytansine (antimitotic) | 0.622 | Maytansine (antimitotic) | 0.615 | Tetraplatin (DNA Alkylating) | 0.961 |

TABLE 1-continued

COMPARE Analysis - Diazonamide in comparison to known anti-mitotic compounds.

| Compound | GI50 (PCC) | Compound | TGI (PCC) | Compound | LC50 (PCC) |
|---|---|---|---|---|---|
| Paclitaxel (antimitotic) | 0.618 | Vincristine (antimitotic) | 0.610 | 5-FUDR (RNA/DNA Anti-Metabolites) | 0.929 |
| Vincristine (antimitotic) | 0.598 | Rhizoxin (antimitotic) | 0.593 | L-Alanosine (RNA/DNA Anti-Metabolites) | 0.815 |

Naturally occurring diazonamide must be isolated from the fractionation of tissues from the marine ascidian, *Diazona angulata*. 256.2 grams of lyophilized ascidian was originally used to collect 54 mg of diazonamide. Lindquist et al. J Am Chem Soc, 1991, 113:2303-2304. Because of the limited availability of the natural compound and its potent antimitotic properties, there have been substantial efforts made to synthesize diazonamides and their intermediates. Vedejs et al. Org. Lett., 2001, 3:2451-2454; Kreisberg et al., Tetrahedron Lett., 2001, 42:627-629; Wipf et al. Org. Lett., 2001, 3:1261-1264; Nicolaou et al., Angew Chem., 2000, 112:3615-3620; Fuerst et al., Org. Lett., 2000, 2:3521-3523; Bagley et al., Tetrahedron Lett., 2000, 41:6897-6900; Bagley et al., Tetrahedron Lett., 2000, 41:6901-6904; Lach et al. Tetrahedron Lett., 2000, 41:6893-6896; Vedejs et al. Org. Lett., 2000, 2:1031-1032; Vedejs et al. Org. Lett., 2000, 2:1033-1035; Magnus et al. Tetrahedron Lett., 2000, 41:831-834; Chan et al., Tetrahedron Lett., 2000, 41:835-838; Hang et al. Synthesis, 1999, 398-400; Magnus et al. Tetrahedron Lett., 1999, 40:451-454; Boto et al. Tetrahedron Lett., 1998, 39:8167-8170; Wipf et al. Tetrahedron Lett., 1998, 39:2223-2226; Jamison, T. F., PhD thesis, Harvard University, Cambridge Mass, 1997; Moody et al. J Chem Soc Perkin Trans, 1996, 16:2413-2419, Moody et al. Pure Appl Chem, 1994, 66:2107-2110; Ritter and Carreira, Angew Chem Int Ed. 2001, 41:2489-2495.

The challenge in synthesizing diazonamide arises from the core of the molecule, comprising a halogenated heterocyclic framework in a single atropisomeric form with a triaryl acetaldehyde and a quaternary C10 center (see 1 and 2, FIG. 1). Various strategies have been used to produce intermediates for diazonamide synthesis. Nicolaou and coworkers directed their effort towards the quaternary C10 center and the heterocyclic core of diazonamide. Nicolaou et al., Angew Chem., 2000, 112:3615-3620; Nicolaou et al., Angew Chem Int Ed, 2000, 39:3473-3478. They employed the Horner-Wadsworth-Emmon cyclization technique to induce ring closure of a benzofuranone-derived intermediate. They also utilized an intramolecular pinacol cyclization strategy of an aldehyde and an oxime. Nicolaou et al., Angew Chem., 2001, 113:4841-4845; Nicolaou et al., Angew Chem Int Ed 2001, 40:4705-4709. Wipf et al. discloses the approach of producing a bis-oxazoyl indole similar to that found in diazonamide A using consecutive Chang rearrangements. The endproduct of this effort does not achieve a ring closed material. Wipf et al., Org. Lett., 2001, 3:1261-1264. Vedejs and coworkers have produced a intermediate with the desired stereochemistry and ring closure using imino-Dieckman cyclization. Vedejs et al. Org. Lett., 2001, 3:2451-2454; Vedejs et al. Org. Lett., 2000, 2:1031-1032; Vedejs et al. Org. Lett., 2000, 2:1033-1035.

In an alternative approach, Magnus et al. disclosed the use of the photo-Fries rearrangement strategy to produce an intermediate that achieves ring closure and exhibits the desired stereochemistry, but does not possess the C 10 quaternary center. Magnus et al. Tetrahedron Lett., 2000, 41:831-834. The aforementioned attempts have not produced compounds with a diazonamide-like skeleton and exhibiting antimitotic activity.

The present invention describes the first successful laboratory synthesis of any diazonamide compound with antimitotic activity. Li et al. "Total synthesis of nominal diazonamides—Part I:Convergent preparation of the structure proposed for (−)-diazonamide A," Angew Chem Int Ed, 2001, 40:4765-4769. The method described herein achieves completely synthetic diazonamide compounds through the combined use of catalytic Heck endocyclization, stereo controlled ring-contracting pinacol rearrangement, and indole arylation via internal photoinduced electron transfer.

SUMMARY OF THE INVENTION

The present invention provides a method of synthesis of a broad class of heterocyclic compounds with anti-mitotic activity. Included in the invention are the compounds, compositions containing the compounds, methods of synthesis, and methods of treatment. These anti-mitotic compounds are useful as anti-proliferative/anti-cancer agents.

The present invention provides novel compounds having the general formula (I):

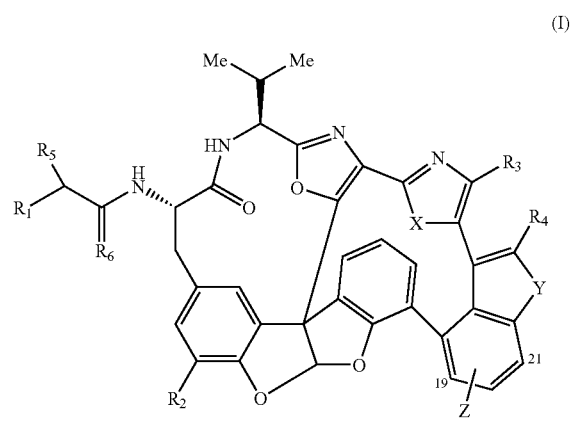

(I)

wherein
$R_1$ is $OR_7$, $NHR_7$;
$R_2$ is H, Cl, Br, or I;
$R_3$ is H, Cl, Br, I, phenyl, ethynyl, straight chain saturated alkyl, or straight chain unsaturated alkyl;
$R_4$ is H, Cl, Br, I, phenyl, ethynyl, straight chain saturated alkyl, or straight chain unsaturated alkyl;
$R_5$ is H, straight chain saturated alkyl, straight chain unsaturated alkyl, branched chain saturated alkyl, branched chain unsaturated alkyl, aryl, or substituted aryl;
$R_6$ is O, NH, or S;
X is O, or S;
Y is O, or $NR_8$;
Z is H, 19-OH, or 21-$OR_8$;
$R_7$ is H, straight chain saturated alkyl, straight chain unsaturated alkyl, acyl, aryl, or heteroaryl; and
$R_8$ is H, straight chain saturated alkyl, straight chain unsaturated alkyl, acyl, or aryl.

The present invention also provides novel compounds having the general formula (II):

(II)

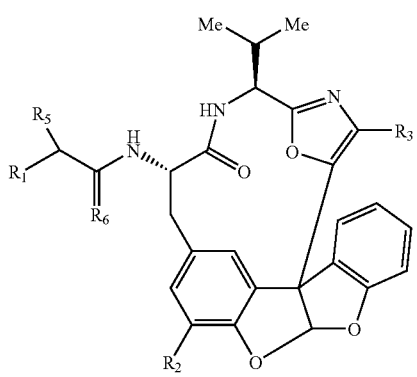

wherein
$R_1$ is $OR_7$, $NHR_7$;
$R_2$ is H, Cl, Br, or I;
$R_3$ is H, CN, or $CO_2R_9$;
$R_5$ is H, straight chain saturated alkyl, straight chain unsaturated alkyl, branched saturated chain alkyl, branched chain unsaturated alkyl, aryl, or substituted aryl;
$R_6$ is O, NH, or S;
$R_7$ is H, straight chain saturated alkyl, straight chain unsaturated alkyl, acyl, aryl, or heteroaryl;
$R_9$ is H, aryl, benzyl, heteroaryl, allyl, straight chain saturated alkyl, straight chain unsaturated alkyl, branched saturated chain alkyl, or branched chain unsaturated alkyl.

The preferred novel compound of this invention (JL-9) is of the following formula (III):

(III)

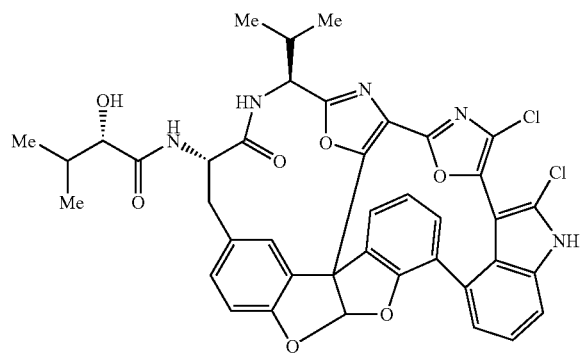

Also included as a preferred novel compound of this invention (JL-10) is of the following formula (IV):

(IV)

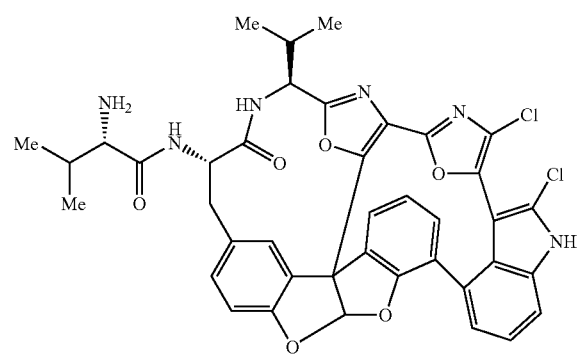

The present invention further provides for novel compounds having the general formula (V):

(V)

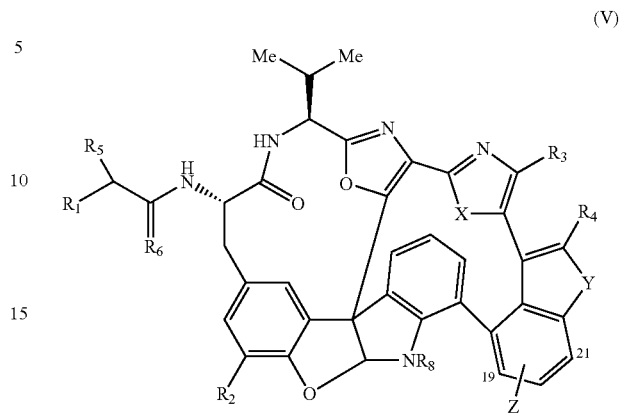

wherein
$R_1$ is $OR_7$, $NHR_7$;
$R_2$ is H, Cl, Br, or I;
$R_3$ is H, Cl, Br, I, phenyl, ethynyl, straight chain saturated alkyl, or straight chain unsaturated alkyl;
$R_4$ is H, Cl, Br, I, phenyl, ethynyl, straight chain saturated alkyl, or straight chain unsaturated alkyl;
$R_5$ is H, straight chain saturated alkyl, straight chain unsaturated alkyl, branched chain saturated alkyl, branched chain unsaturated alkyl, aryl, or substituted aryl;
$R_6$ is O, NH, or S;
X is O, or S;
Y is O, or $NR_8$;
Z is H, 19-OH, or 21-$OR_8$;
$R_7$ is H, straight chain saturated alkyl, straight chain unsaturated alkyl, acyl, aryl, or heteroaryl; and
$R_8$ is H, straight chain saturated alkyl, straight chain unsaturated alkyl, acyl, or aryl.

The present invention further provides for novel compounds having the general formula (VI):

(VI)

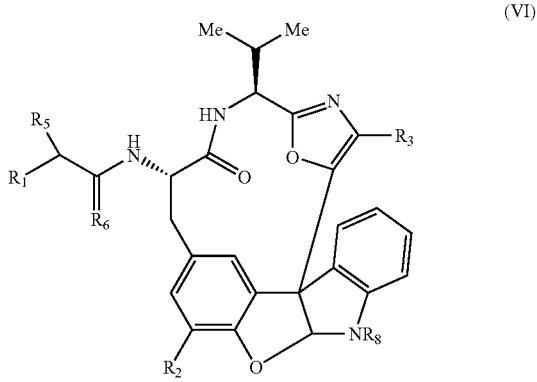

wherein
$R_1$ is $OR_7$, $NHR_7$;
$R_2$ is H, Cl, Br, or I;
$R_3$ is H, CN, or $CO_2R_9$;
$R_5$ is H, straight chain saturated alkyl, straight chain unsaturated alkyl, branched saturated chain alkyl, branched chain unsaturated alkyl, aryl, or substituted aryl;
$R_6$ is O, NH, or S;
$R_7$ is H, straight chain saturated alkyl, straight chain unsaturated alkyl, acyl, aryl, or heteroaryl;

$R_8$ is H, straight chain saturated alkyl, straight chain unsaturated alkyl, acyl, aryl;

$R_9$ is H, aryl, benzyl, heteroaryl, allyl, straight chain saturated alkyl, straight chain unsaturated alkyl, branched saturated chain alkyl, or branched chain unsaturated alkyl.

The present invention is also directed to methods of synthesizing diazonamide and its analogs. The method comprises the steps of a) A, E and F-ring assembly (see 2, FIG. 1), b) Heck endocyclization, c) Ring-contracting pinacol rearrangment and d) internal indole arylation via photo-induced electron transfer cyclization.

The present invention also provides for a method of inhibiting the growth of a proliferating cell in a subject comprising administering to the subject of a compound of the formula (I), (II), (III), (IV), (V) or (VI) in an amount sufficient to inhibit the growth of the proliferating cell.

The present invention also provides for a method of inhibiting the growth of a tumor cell in a subject comprising administering to the subject of a compound of the formula (I), (II), (III), (IV), (V) or (VI) in an amount sufficient to inhibit the growth of the proliferating cell.

The compounds of the present invention described herein may be formulated into composition comprising carriers, excipients, and materials conventionally used in the production of pharmaceutical compositions.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE INVENTION

The present invention relates to a broad class of heterocyclic compounds with anti-mitotic activity, diazonamide compounds and their analogs. The present invention also provides a method of synthesis of diazonamide compounds and their analogs. These anti-mitotic compounds are useful as anti-proliferative/anti-cancer agents.

Figure 1:
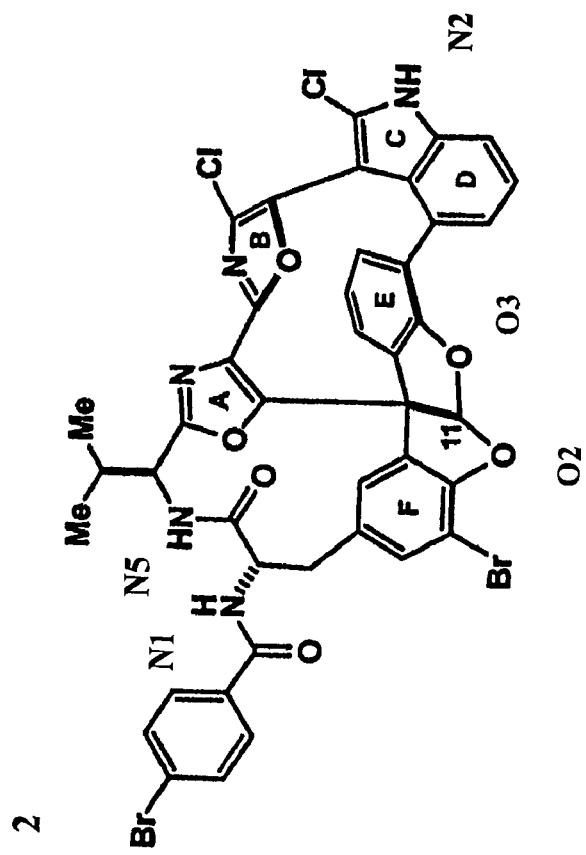
FIG. 1 shows the initial diazonamide structure assignments.
Figure 1:
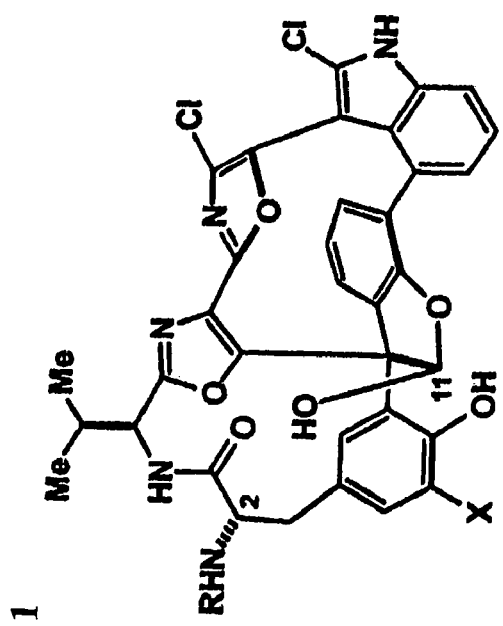
Figure 2:
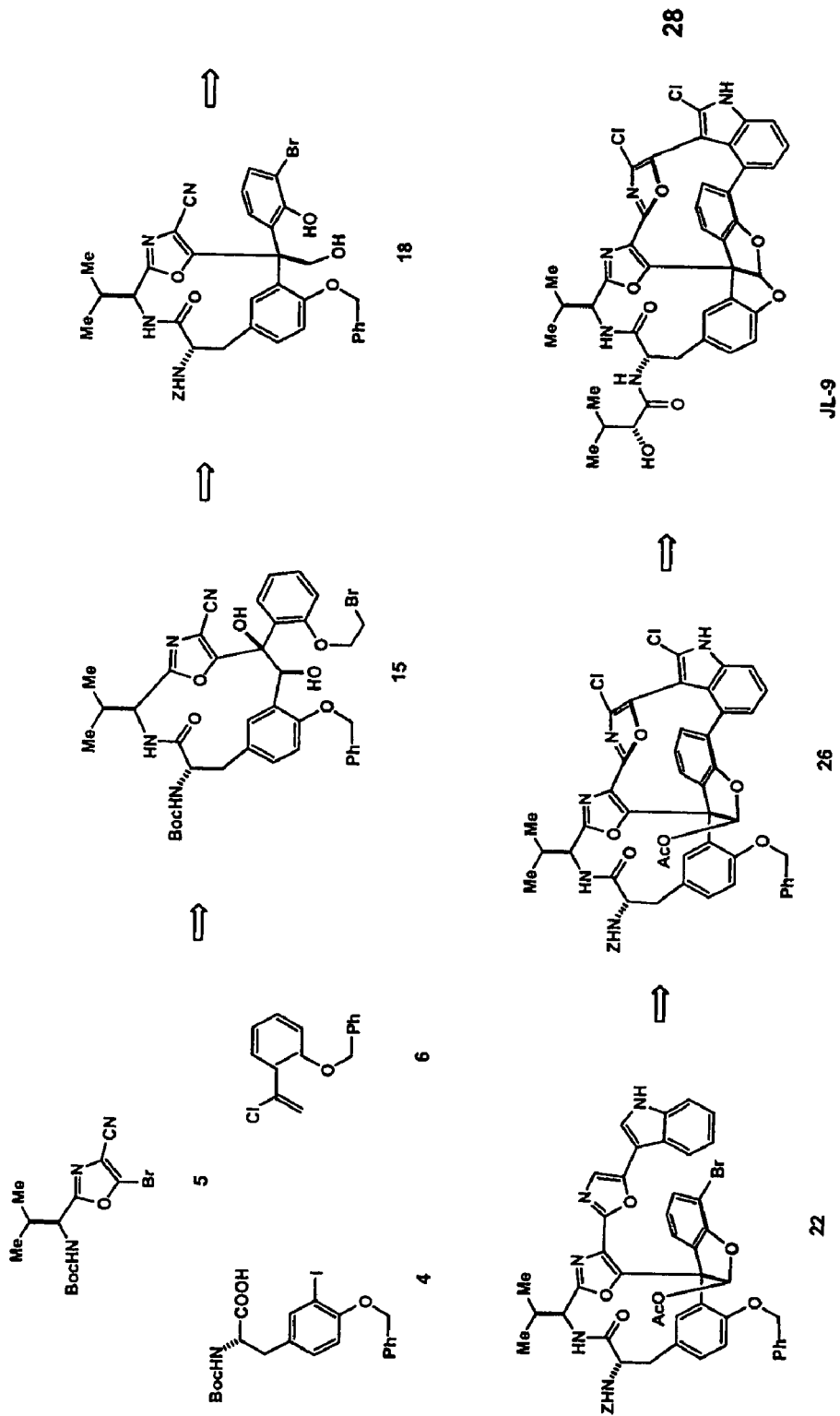
FIG. 2 shows the general scheme for diazonamide synthesis.

In an embodiment of the invention, a method of synthesizing diazonamide compounds of formula (I), (II), (III), and (IV) is disclosed in accordance with the reaction scheme of FIG. 2 and further described in Example 1. The method of synthesis comprises generally the steps of a) A, E and F-ring assembly (see 2, FIG. 1), b) Heck endocyclization, c) Ring-contracting pinacol rearrangment and d) internal indole arylation via photo-induced electron transfer cyclization.

The practice of the present invention employs, unless otherwise indicated, conventional techniques of synthetic organic chemistry, protein chemistry, molecular biology, microbiology, and recombinant DNA technology, which are well within the skill of those in the art. Such techniques are explained fully in the literature. See, e.g., Scopes, R. K., Protein Purification Principles and Practices, 2d ed. (Springer-Verlag, 1987), Methods in Enzymology (S. Colowick and No. Kaplan, eds., Academic Press, Inc.), Sambrook et al., Molecular Cloning: A Laboratory Manual, 2d ed., Cold Spring Harbor Press, Cold Spring Harbor, N.Y., 1989, Handbook of Experimental Immunology, Vols. I-IV (D. M. Weir and C. C. Blackwell, eds., 1986, Blackwell Scientific Publications); House, Modern Synthetic Reactions, 2d ed., Benjamin/Cummings, Menlo Park, Calif., 1972.

Figure 3:
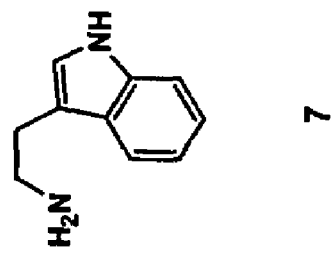
FIG. 3 shows the structures of the starting components for diazonamide synthesis.
Figure 3:
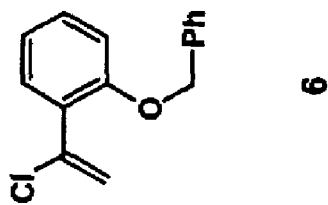
Figure 3:
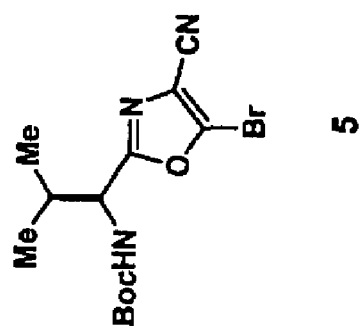
Figure 3:
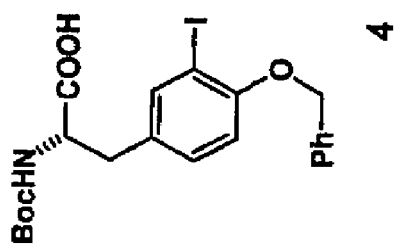
Figure 3:
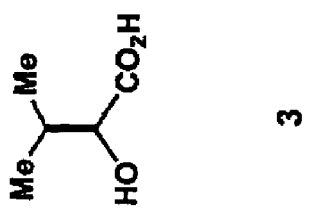

FIG. 3 shows the structures of the initial components for diazonamide synthesis described herein. Tyrosine derivative 4 and bromide 5 exhibit protecting groups, N-Boc (or tert-butoxycarbonyl). Other carbamate protecting groups also suitable include trimethylsiloxycarbonyl (TeOC); benzyloxycarbonyl (CBz); and fluorenyl methyloxycarbonyl (FMoc).

Figure 4:
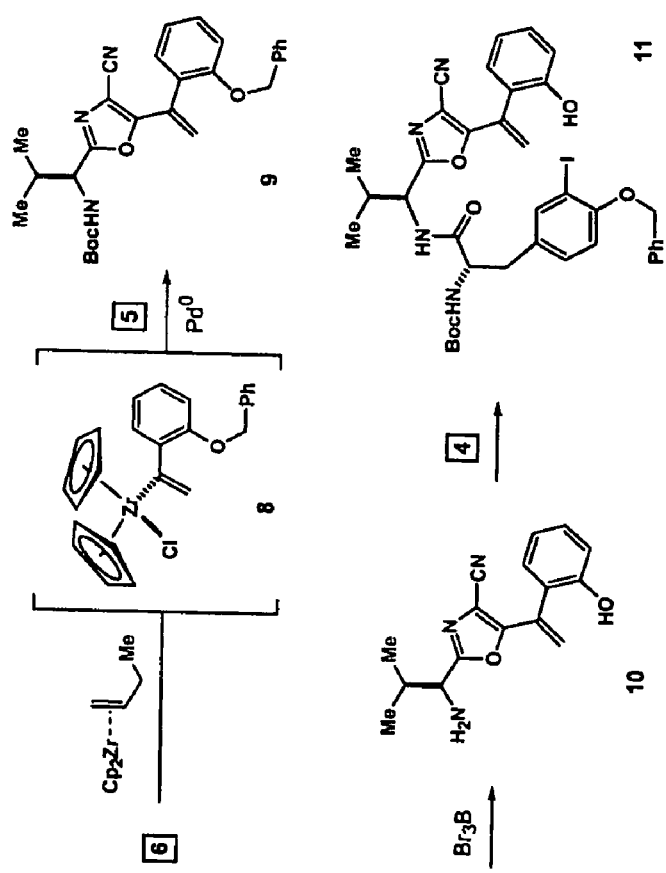
FIG. 4 shows the early assembly steps of diazonamide synthesis.

In an embodiment of the invention, the structure 9 is prepared by a palladium catalyzed cross coupling reaction, also known as a Negishi coupling reaction (FIG. 4). Negishi et al. Tetrahedron Lett, 1986, 27:2829-2832. A particularly useful variation of Takahashi's modification of a Negishi coupling reaction may be employed, which does not require a Zr-to-Zn transmetalation prior to the addition of the electrophile. Takahashi et al. J Am Chem Soc, 1995, 117:11039, 11040. In place of chloride 6, the corresponding styrylstannone, e.g. trimethyl or tributyl may be used (Stille coupling) or styroboronic acid (boronic ester) may be used. Lastly compounds of type 9 can be prepared by a carbonylative coupling between oxazoyl bromide 5, a molecule of carbon monoxide, and a suitable E ring nucleophile (e.g. o-benzyl-1-trimethylstanylphenol.)

Dibutylzirconocene is treated with α-chlorostyrene 6 in the presence of a solvent to generate species 8 (FIG. 4). Dibutylzirconocene is generated in situ by treatment of commercial zirconacene dichloride with n-butyl lithium. Preferably, a reduced form of dibutylzirconocene is utilized to show its interaction with α-chlorostyrene 6 as an oxidative addition. Suitable solvents may include ether, dimethoxyethane, or preferably tetrahydrofuran. The aforementioned reaction occurs at a temperature of between −80° C. and −70° C., preferably −78° C., for several hours, preferably three hours.

The regiodefined vinyl $Zr^{IV}$ species 8 is coupled with bromide 5 in the presence of a palladium catalyst to generate species 9 (FIG. 4). Suitable palladium catalysts include various palladium (0) salts and palladium (II) salts, such as palladium tetrakis (triphenylphosphine), dipalladium tris (dibenzylidene acetone) and palladium diacetate. The optimum condition utilizes a catalyst generated by pretreatment of palladium (II) acetate with tri-o-tolylphosphine (1:1 Pd:phosphine). The aforementioned reaction is incubated at a temperature of between 20° C. and 40° C., preferably room temperature, for several hours, preferably 8 hours.

The protecting groups found on species 9 may be removed to produce amine 10 in the presence of a solvent. Suitable solvents may include 1,2 dichloroethane, or preferably dichloromethane. The aforementioned reaction is run at a temperature of between −78° C. and −20° C., preferably beginning the reaction at −78° C. and allowing the reaction to warm to room temperature, for several hours, preferably 1.5 hours. Conditions for the removal of the protecting groups are well known to those familiar to the art of organic synthesis; e.g. hydrogenation to remove benzyl or benzyloxycarbonyl, a fluoride source (such as tetrabutylammonium fluoride) to remove silyl-based blocking groups, an acid source (such as trifluoroacetic acid) to remove tert-butoxycarbonyl or 4-methoxybenzyl, etc.

Referring to FIG. 4, a tyrosine derivative 4 is condensed with species 10 in the presence of a solvent, a peptide coupling agent, and a mildly basic additive, such as puridine, triethylamine, morpholine, or preferably, diisopropylamine, to generate dipeptide 11. Suitable solvents may include ether, or preferably DMF (dimethylformamide). Suitable coupling reagents include HBTU (O-(1H-benzotriazole-1-yl)-N,N,N', N'-tetramethyluronium hexafluorophosphate), various carbodiimides (e.g. dicyclohexocarbodiimide, diisopropylcarbodiimide), in the presence of HOBt (N-Hydroxybenzotriazole) or preferably TBTU (2-(1H-benzotriazol-1-yl)-1,1,3,3-tetramethyluronium tetrafluoroborate).

Figure 5:
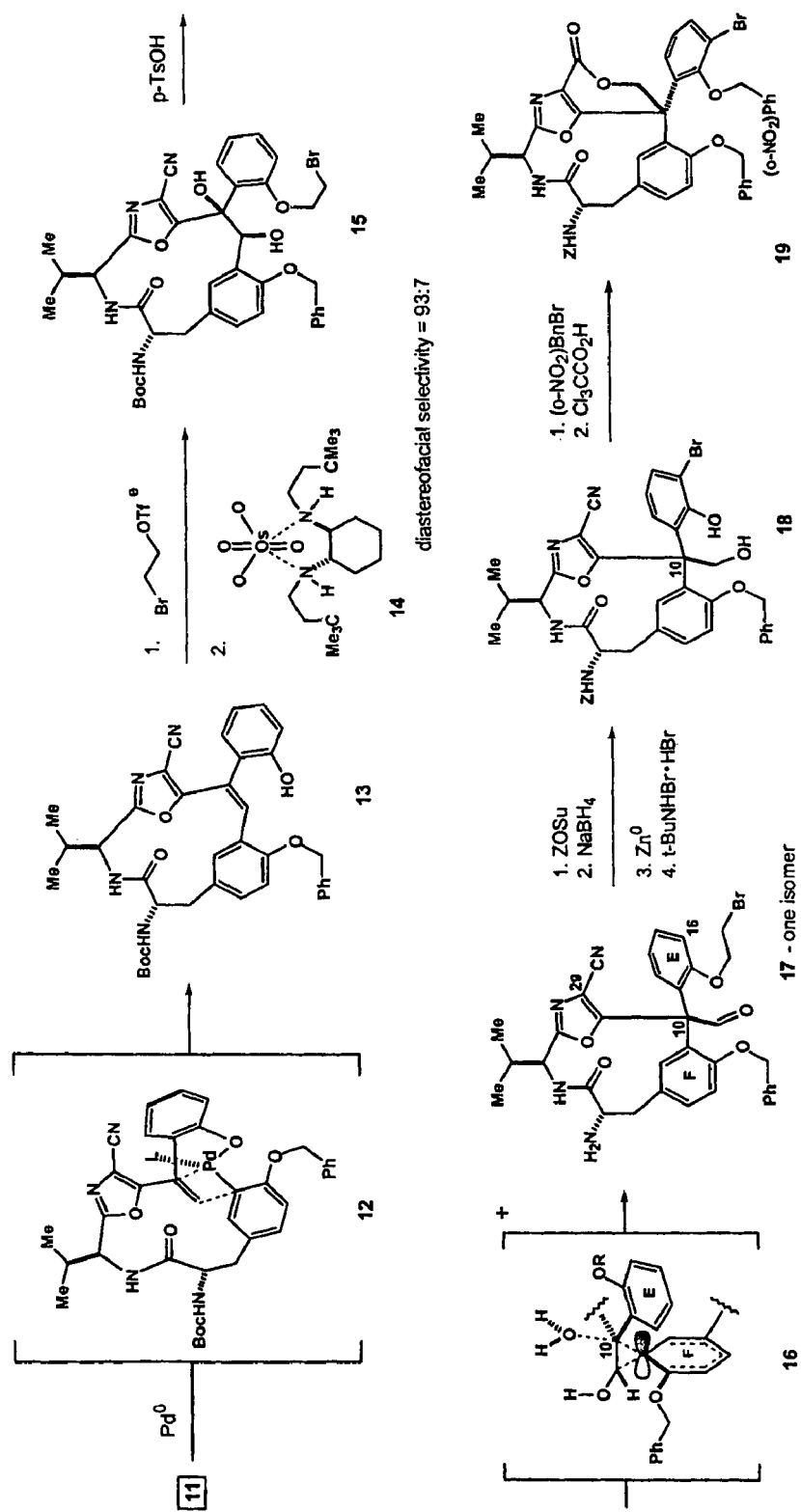
FIG. 5 shows the Heck endocylization and ring contracting pinacol rearrangement steps of diazonamide synthesis.

Referring to FIG. 5, a Heck endocyclization reaction induces the formation of macrolactam 13. The reaction is catalyzed by palladium in the presence of solvent, $Ag_3PO_4$, and a phosphene ligand. Suitable palladium catalysts include palladium (0) and palladium (II) precatalysts, such as palladium tetrakis (triphenylphosphine), or dipalladium tris (dibenzylidene acetone). Phosphene additives, in general, inhibit the reactions, although 2-(di-tert-butylphosphanyl)biphenyl is used effectively; presumably not interacting with a templating effect (e.g. structure 12) thought to facilitate cyclization while still maintaining a soluble robust catalyst system by ligation of the metal. Suitable solvents may include dimethoxyethane, DMF, p-dioxane, or preferably tetrahydrofuran. The aforementioned reaction occurs at a temperature of between 60° C. and 90° C., preferably 75° C., for several hours, preferably eight hours. $Ag_3PO_4$ serves to scavenge HI (hydroiodic acid) produced by the process. Other potentially applicable agents for this purpose include tertiary amines (triethylamine) and alkaline metal carbonates (e.g. K2CO3). Those familiar with the state of the art will recognize the large number of available methods to induce Heck endocyclization.

The C16 phenol of macrolactam 13 is derivatized as its 2-bromoethyl ether e in the presence of solvent, 2-bromoethyltriflate, and potassium t-butoxide, and subsequently subjected to oxidation in the presence of a dihydroxylation agent, solvent, followed by $H_2S$ to generate glycol 15. The dihydroxylation agent is an osmium reagent 14 preferably formed from osmium tetroxide and (1S,2S)-N,N'-bis(3,3-dimethylbutyl)-cyclohexane-1,2-diamine. The use of the osmium agent is required to override the intrinsic bias of the molecule to undergo hydroxylation with opposite face selectivity and ensure correct stereochemistry. The aforementioned reaction occurs at a temperature of between −60° C. and −30° C., preferably −50° C., for four hours. Hydrogen sulfide gas is introduced to the reaction to decompose the first formed osmium glycolate, thereby liberating the free vicinal diols.

Referring to FIG. 5, glycol 15 is subjected to a ring contracting pinacol rearrangement under acidic conditions in the presence of p-TsOH to obtain the triaryl acetaldehyde 17 through a proposed bridging phenolium intermediate 16. The aforementioned reaction occurs at a temperature of between 80° C. and 100° C., preferably 95° C., for several minutes, preferably 40 minutes. The p-TsOH should be added in three equal portions at ten minute intervals during the first thirty minutes of the reaction.

The C2 amine of triaryl acetaldehyde 17 is carbamoylated, preferably with $PhCH_2OCO_2Su$) at room temperature (Su=N-succinimidyl). The C10 aldehyde is reduced in the presence of $NaBH_4$, and $CeCl3$, the 2-bromoethyl ether is degraded with excess Rieke zinc at 0° C., and the E-ring phenol produced is ortho-brominated in the presence of $tBuNH_2/Br_2$ complex to obtain 18.

The more acidic nucleophile in 18, (the phenol) is reetherified with o-nitro-benzylbromide (using a weak base to generate a phenoxide nucleophile) (FIG. 5). The product is subsequently stirred with preferably moist trichloroacetic acid to generate a lactone 19. Other acids able to induce this internal nitrile alkoxylation include p-TsOH, dichloroacetic acid or methane sulfonic acid.

Figure 6:
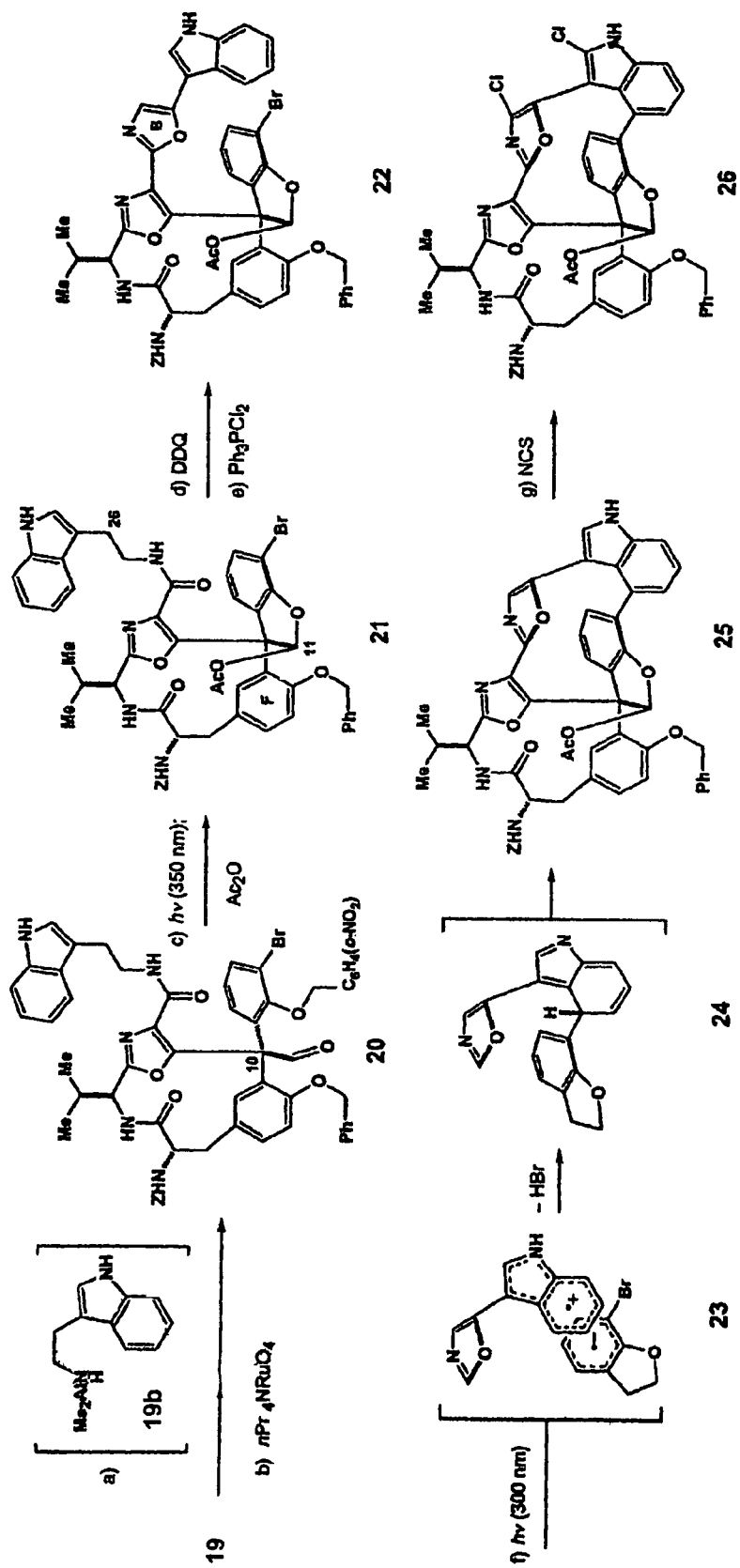
FIG. 6 shows indole arylation via photo-induced electron transfer.

Referring to FIG. 6, lactone 19 is opened with a tryptamine-derived methylaluminum amide 19b. A series of 10 steps are carried out to produce the aryl bromide 20.

The alcohol produced by the reaction is then oxidized with tetrapropyl ammonium perrhuthenate (TPAP) catalyst in the presence of stoichiometric amounts of n-methyl morpholine N-oxide (NMO) to give aldehyde 20. Aldehyde 20 can also be produced from 19 using a three step sequence of lactone hydrolysis, Dess Martin periodinane oxidation, and peptide coupling with tryptamine. Li et al., "Synthetic seco forms of (−)-Diazonamide A," Angew Chem Int Ed, 2001, 40:2682-2685.

Aldehyde 20 is briefly photolyzed (350 nm, rayonet apparatus) in dilute dioxane solution (3 mM) to provide a crude C11 hemiacetal which is then acetylated with acetic anhydride (catalytic dmat, dichloromethane solvent) to afford a single diastereomer of acetate 21 (FIG. 6). Techniques for photolytic decomposition of the ortho-nitrobenzo-based protecting groups are familiar in the state of the art.

A two-step oxidation/cyclodehydration protocol manipulates the acyl tryptamine segment of 21 into bis(oxazoyl) indole 22. These steps comprise subjecting 21 to DDQ (2,3-dichloro-5,6-dicyano-1,4-benzoquinone) oxidation to generate a C26 aryl ketone. This β-kyl amide is then cyclodehydrated using $(Cl_3C)_2$, $Ph_3P$, and $Et_3N$ to afford 22. Wipf et al. Tetrahedron Lett, 1998, 39:2223-2226. The dehydration procedure can use iodine in place of $(Cl_3C)_2$, or, alternatively, preformed $Ph_3PBr_2$ can be substituted for the entire $(Cl_3C)_2$, $Ph_3P$, and $Et_3N$.

UV irradiation of degassed solutions of 22 (300 nm, 5.0× $10^{-3}$M in 3:1 $CH_3CN/H_2O$) results in loss of HBr and the formation of internal acylation product 25 (FIG. 6). A single regioisomeric biaryl (one atropdiastereomer) is isolated from this reaction although there is competing production of uncyclized materials lacking bromine. One mechanism to interpret this Witkop-type cyclization invokes intramolecular photo-induced electron transfer from the indole chromophore to the adjacent bromo arene. Mesolytic elimination of bromide from the resultant radical-ion pair 23, biradical collapse, and prototropy in 4H-indole 24 would give 25.

To produce the dichloride 26, 25 is oxidized in the presence of 2:1 equivalence N-chlorosuccinimide (NCS) in a mixture of the THF and carbon tetrachloride as solvent. Commercial trichloroisocyanuric acid may substitute for NCS in this reaction (FIG. 6).

Dichloride 26 undergoes partially hydrogenolysis under an atmosphere of hydrogen in the presence of palladium on charcoal catalyst in an alcohol solvent. The amine produced is reacylated with Z-L-Val-OH using TBTU as a coupling in DMS solvent. Stannoxane-catalyzed deacetylation of the acetyl hemiacetal and a final hydrogenolysis provides the structure originally proposed for (−)-diazonamide A 1b.

Figure 7:
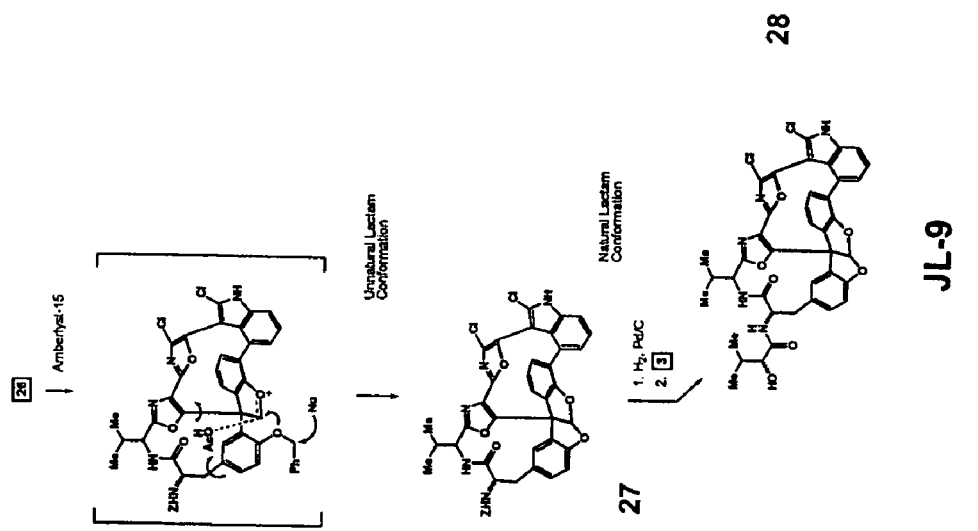
FIG. 7 shows the final assembly steps of diazonamide synthesis.

Amberlyst-15 acidic resin is mediates dealkylative C11 acetal formation (FIG. 7). The benzyl carbamate of the product formed (27) is hydrogenolyzed and the free C2 amine produced acylated with L-α-hydroxy isovaleric acid using diethylphosphoryl cyanide as a coupling reagent to provide JL-9 28 (FIG. 7).

After synthesis of the diazonamide compounds, the inventors performed subsequent analysis on the synthesized compounds as further described in Example 2. The synthetic material was remarkably unstable and its proton NMR spectrum differed from the spectrum of naturally occurring diazonamide. Further studies indicated that the C2 sidechain had been misassigned in the original characterization and that structure 2 (FIG. 1) was also misassigned based in improper interpretation of X-ray crystallographic data. Li et al., "Total synthesis of nominal diazonamides-Part 2: On the true structure and origin of natural isolates," 2001, Angew Chem Int Ed, 40:4770-4773. Taken together, and in light of 2-D NMR data from a trace sample of natural diazonamide A (FIG. 10), the inventors have further characterized the naturally occurring diazonamides as described in Example 3 and in formulas (V) and (VI).

Figure 11:
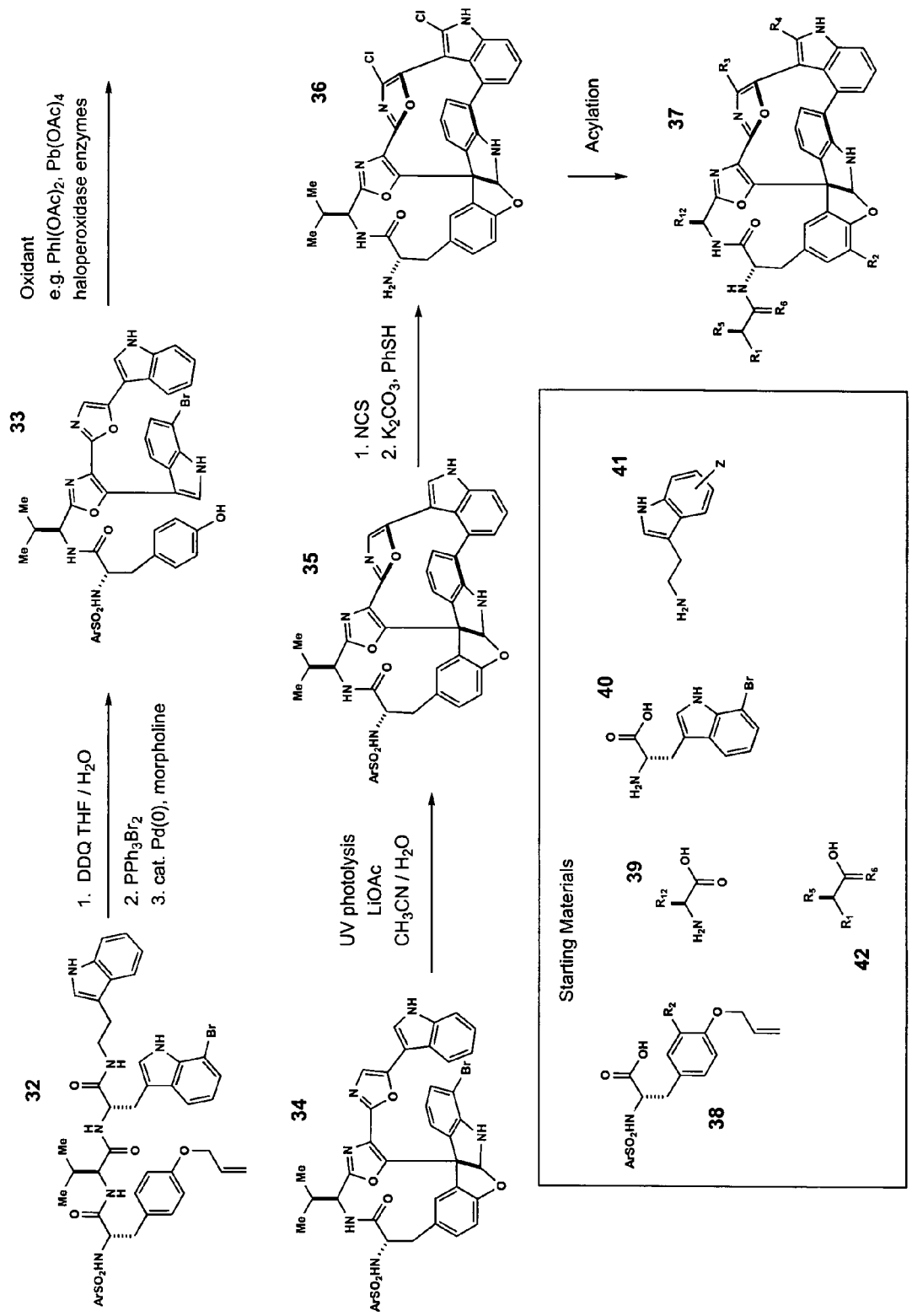
FIG. 11 shows the general scheme for synthesis of revised diazonamide structures.
Figure 12:
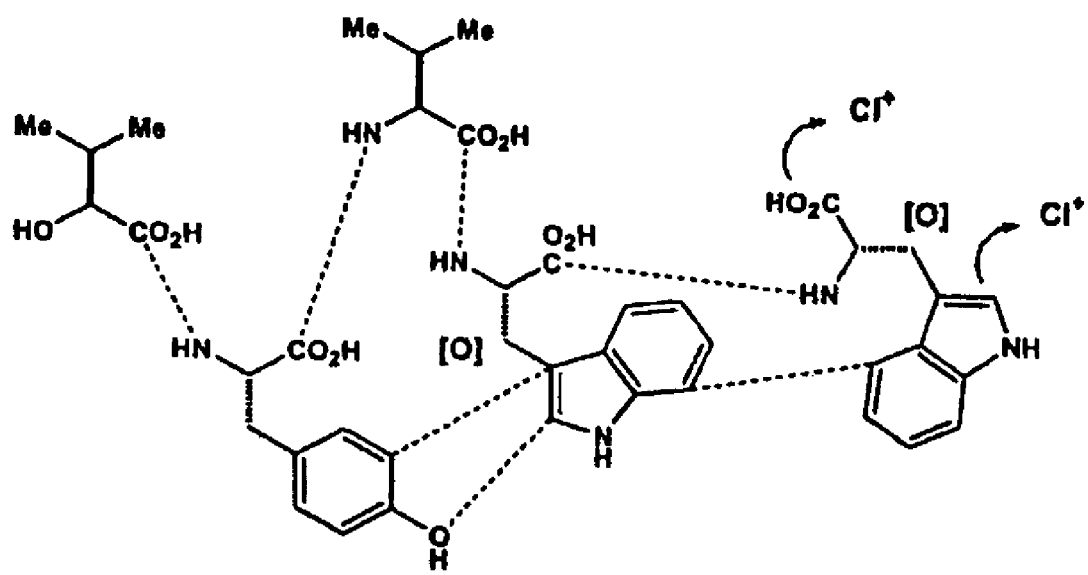
FIG. 12 shows a scheme for the biosynthetic origin of revised diazonamide compounds.

In another embodiment of the invention, a method of synthesizing diazonamide compounds of formula (V) and (VI) is disclosed in accordance with the reaction scheme of FIG. 11 and further described in Example 3. The revised structure assigned to diazonamide A 30 (FIG. 9) indicates a direct lineage between its polycyclic structure and common amino acid components (FIG. 12). Moreover, its synthesis can be approached by, in essence, remolding of a linear oligomeric precursor. Referring to FIG. 11, polyamide 32 may be assembled by standard F-Moc-based peptide synthesis beginning with compounds 38-41. Treatment of 32 with excess (4-5 equivalence) DDQ may oxygenate the 2 indole benzylic positions to provide a diaryl ketone. This product then undergoes a double cyclodehydration when exposed to Ph3PBr2 in dichloromethane solvent. Removal of the allyl protecting groups in the bis(oxazoyl)indole product will then provide phenol 33 (FIG. 11). A 2-electron oxidation of 33 using, for example, an iodine (III) reagent initiates a cyclization between an electron-deficient intermediate and the adjacent indole halo sidechain (as indicated) to afford 34. This substance may be photocyclized to a complete diazonamide skeleton 35 in a manner directly analogous to that used in the synthesis of 25 from 22 (see FIG. 6). Cleavage of the o-nitrophenylsulphonamide protecting group of 35 with a sulfur nucleophile provides 36 *a*. Chlorination of 35 with n-chlorosuccinimide and cleavage of the o-nitrophenylsulphonamide protecting group with a sulfur nucleophile provides 36. The free amine can be acetylated with S-α-hydroxyisovaleric acid to provide 30a and diazonamide A 30. Moreover, beginning with components having varied substitutes as well as using alternative acetylating agents 42, a great many variants of a diazonamide will be available (37, 37a).

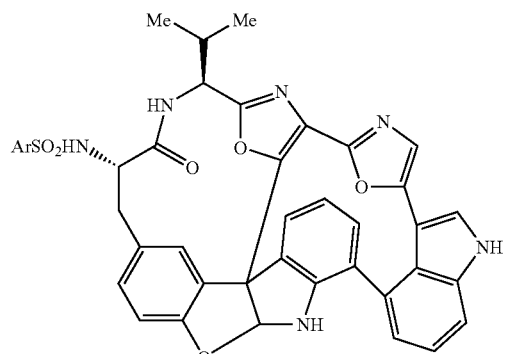

35

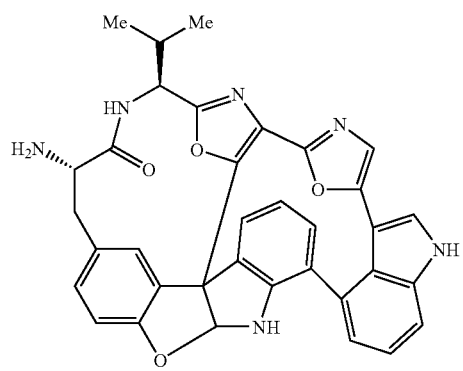

36a

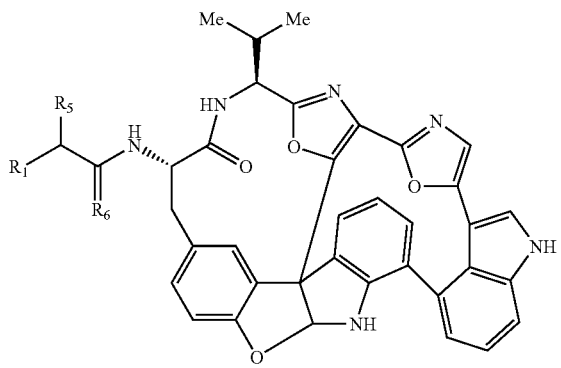

37a

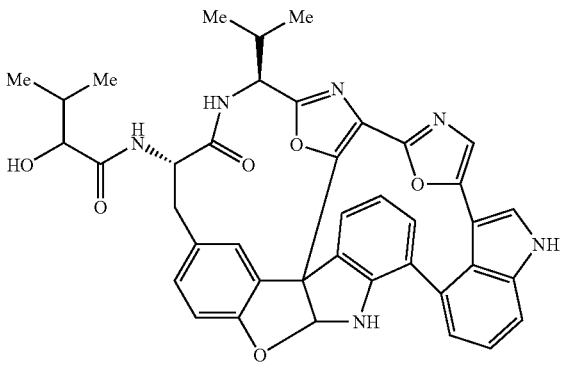

30a

The compounds of the present invention have been shown to inhibit mitosis and cellular proliferation as determined using various cell lines, including tumor cell lines such as SK-MEL-5 (a human melanoma cell line), OVCAR 3 (a human adenocarcinoma cell line), and HCT-116 (a human colorectal carcinoma cell line), as described in Examples 5 and 6. Compounds of the present invention, when applied to cells in culture, inhibit proliferation of cells by reducing the number of viable cells in treated versus untreated cultures. Furthermore, the compounds of the present invention have been shown to arrest cell populations in mitosis in a manner similar to known antimitotic agents such as taxol and vinblastine (Example 6). In view of these aforementioned properties, it is contemplated that the compounds of the invention may be used to inhibit mitosis or cell division upon administration to dividing cell populations.

One aspect of the invention is a method of regulating cell growth and proliferation in normal and malignant cells, comprising the step of administering, to the cells, a compound of the present invention in an amount effective to regulate cell growth and proliferation.

Another aspect of the present invention is a method of inhibiting growth of proliferating cells comprising the step of administering, to the proliferating cells a compound of the present invention in an amount effective to inhibit growth or mitosis of the proliferating cell.

In addition, the compounds of the invention are useful in the treatment of diseases in which inhibition of cell growth or proliferation is desired.

Another aspect of the invention is a method for inhibiting the growth of tumor cells by contacting a tumor cell within a subject with a compound of the present invention under conditions permitting the uptake of said compound by said tumor cell and proliferation of the cell is inhibited. The tumor cell may be derived from a tissue selected from the group consisting of brain, lung, liver, spleen, kidney, lymph node, small intestine, blood, pancreas, colon, stomach, breast, endometrium, prostate, testicle, ovary, skin, head, and neck, esophagus, and bone marrow. The subject is preferably a mammal, more preferably human. In an embodiment, the compound is contained within a liposome. In yet another embodiment, the compound is administered intratumorally, in the tumor vasculature, locally to the tumor, regionally to the tumor, or systemically. In a further embodiment, the method comprises administering a second chemotherapeutic agent to said subject. In a further embodiment, the second chemotherapeutic agent may be cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, farnesyl-protein transferase inhibitors, transplatinum, 5-fluorouracil, vincristin, vinblastin and methotrexate or any analog or derivative variant of the foregoing. In another embodiment, the method further comprises administering radiation to said subject. In another embodiment, the radiation is delivered local to a cancer site. In yet another embodiment, the radiation is whole body radiation. The radiation may be γ-rays, X-rays, accelerated protons, microwave radiation, UV radiation or the directed delivery of radioisotopes to tumor cells. In another embodiment, the method further comprises administering an anticancer gene to said subject. In an embodiment of the invention, the anticancer gene is a tumor suppressor. In another embodiment of the invention, the anticancer gene is an inhibitor of apoptosis. In another embodiment of the invention, the anticancer gene is an oncogene antisense construct.

A further aspect of the invention is a method for altering the phenotype of a tumor cell comprising the step of contacting the cell with a compound of the present invention, under conditions permitting the uptake of said compound by said tumor cell. The tumor cell may be derived from a tissue selected from the group consisting of brain, lung, liver, spleen, kidney, lymph node, small intestine, blood, pancreas, colon, stomach, breast, endometrium, prostate, testicle, ovary, skin, head, and neck, esophagus, and bone marrow. In an embodiment of the invention, the phenotype is selected from the group consisting of proliferation, migration, contact inhibition, soft agar growth, cell cycling, invasiveness, tumorigenesis, and metastatic potential. In another embodiment of the invention, the compound may be contained within a liposome.

Another embodiment of the invention is a method of treating a subject with cancer comprising administering to said subject a compound of the present invention under conditions permitting the uptake of said compound by said cancer cell, wherein proliferation of the cell is inhibited. In an embodiment of the invention, the subject is human.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

The present invention also provides for physiological compositions comprising the compounds of the present invention. Aqueous physiological compositions of the present invention comprise an effective amount of a compound of the present invention or pharmaceutically acceptable salt thereof, dissolved and/or dispersed in a pharmaceutically acceptable carrier and/or aqueous medium.

The phrases "physiologically, pharmaceutically and/or pharmacologically acceptable" refer to molecular entities and/or compositions that do not produce an adverse, allergic and/or other untoward reaction when administered to an animal.

As used herein, "physiologically and/or pharmaceutically acceptable carrier" includes any and/or all solvents, dispersion media, coatings, antibacterial and/or antifungal agents, isotonic and/or absorption delaying agents and/or the like. The use of such media and/or agents for pharmaceutical active substances is well known in the art. Except insofar as any conventional media and/or agent is incompatible with the active ingredient, its use in the therapeutic compositions is contemplated. Supplementary active ingredients can also be incorporated into the compositions. For human administration, preparations should meet sterility, pyrogenicity, general safety and/or purity standards as required by FDA Office of Biologics standards.

The biological material should be extensively dialyzed to remove undesired small molecular weight molecules and/or lyophilized for more ready formulation into a desired vehicle, where appropriate. The active compounds may generally be formulated for parenteral administration, e.g., formulated for injection via the intravenous, intramuscular, sub-cutaneous, intralesional, and/or even intraperitoneal routes. The preparation of aqueous compositions that contain a therapeutically effective, amount of the compounds of the invention or physiologically acceptable salts thereof as an active component and/or ingredient will be known to those of skill in the art in light of the present disclosure. Typically, such compositions can be prepared as injectables, either as liquid solutions and/or suspensions; solid forms suitable for using to prepare solutions and/or suspensions upon the addition of a liquid prior to injection can also be prepared; and/or the preparations can also be emulsified.

Pharmaceutical forms suitable for injectable use include sterile aqueous solutions and/or dispersions; formulations including sesame oil, peanut oil and/or aqueous propylene glycol; and/or sterile powders for the extemporaneous preparation of sterile injectable solutions and/or dispersions. In all cases the form must be sterile and/or must be fluid to the extent that easy syringability exists. It must be stable under the conditions of manufacture and/or storage and/or must be preserved against the contaminating action of microorganisms, such as bacteria and/or fungi.

Solutions of the active compounds as free base and/or physiologically acceptable salts can be prepared in water suitably mixed with a surfactant, such as hydroxypropylcellulose. Dispersions can also be prepared in glycerol, liquid polyethylene glycols, and/or mixtures thereof and/or in oils. Under ordinary conditions of storage and/or use, these preparations contain a preservative to prevent the growth of microorganisms.

Compounds of the present invention can be formulated into a composition in a neutral and/or salt form. Pharmaceutically acceptable salts, include the acid addition salts and/or which are formed with inorganic acids such as, for example, hydrochloric and/or phosphoric acids, and/or such organic acids as acetic, oxalic, tartaric, mandelic, and/or the like.

The carrier can also be a solvent and/or dispersion medium containing, for example, water, ethanol, polyol (for example, glycerol, propylene glycol, and/or liquid polyethylene glycol, and/or the like), suitable mixtures thereof, and/or vegetable oils. The proper fluidity can be maintained, for example, by the use of a coating, such as lecithin, by the maintenance of the required particle size in the case of dispersion and/or by the use of surfactants. The prevention of the action of microorganisms can be brought about by various antibacterial and/or antifungal agents, for example, parabens, chlorobutanol, phenol, sorbic acid, thimerosal, and/or the like. In many cases, it will be preferable to include isotonic agents, for example, sugars and/or sodium chloride. Prolonged absorption of the injectable compositions can be brought about by the use in the compositions of agents delaying absorption, for example, aluminum monostearate and/or gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the required other ingredients from those enumerated above. In the case of sterile powders for the preparation of sterile injectable solutions, the preferred methods of preparation are vacuum-drying and/or freeze-drying techniques which yield a powder of the active ingredient plus any additional desired ingredient from a previously sterile-filtered solution thereof. The preparation of more, and/or highly, concentrated solutions for direct injection is also contemplated, where the use of DMSO as solvent is envisioned to result in extremely rapid penetration, delivering high concentrations of the active agents to a small tumor area.

Upon formulation, solutions will be administered in a manner compatible with the dosage formulation and/or in such amount as is therapeutically effective. The formulations are easily administered in a variety of dosage forms, such as the type of injectable solutions described above, but drug release capsules and/or the like can also be employed.

For parenteral administration in an aqueous solution, for example, the solution should be suitably buffered if necessary and/or the liquid diluent first rendered isotonic with sufficient saline and/or glucose. These particular aqueous solutions are especially suitable for intravenous, intramuscular, subcutaneous and/or intraperitoneal administration. In this connection, sterile aqueous media which can be employed will be known to those of skill in the art in light of the present disclosure. For example, one dosage could be dissolved in 1 ml of isotonic NaCl solution and/or either added to 1000 ml of hypodermoclysis fluid and/or injected at the proposed site of infusion, (see for example, "Remington's Pharmaceutical Sciences" 15th Edition, pages 1035-1038 and/or 1570-1580). Some variation in dosage will necessarily occur depending on the condition of the subject being treated. The person responsible for administration will, in any event, determine the appropriate dose for the individual subject.

The compounds of the present invention may be formulated within a mixture to comprise about 0.0001 to 1.0 milligrams, and/or about 0.001 to 0.1 milligrams, and/or about 0.1 to 1.0 and/or even about 10 milligrams per dose and/or so. Multiple doses can also be administered.

Various routes of administration are contemplated for various tumor types. For practically any tumor, systemic delivery is contemplated. This will prove especially important for attacking microscopic or metastatic cancer. Where discrete tumor mass may be identified, a variety of direct, local and regional approaches may be taken. For example, the tumor may be directly injected with the compound. A tumor bed may be treated prior to, during or after resection. Following resection, one could deliver the compound by a catheter left in place following surgery. One may utilize the tumor vasculature to introduce the compound into the tumor by injecting a supporting vein or artery. A more distal blood supply route also may be utilized.

In addition to the compounds formulated for parenteral administration, such as intravenous and/or intramuscular injection, other pharmaceutically acceptable forms include, e.g., tablets and/or other solids for oral administration; liposomal formulations; time release capsules; and/or any other form currently used, including cremes.

Oral formulations include such normally employed excipients as, for example, pharmaceutical grades of mannitol, lactose, starch, magnesium stearate, sodium saccharine, cellulose, magnesium carbonate and/or the like. These compositions take the form of solutions, suspensions, tablets, pills, capsules, sustained release formulations and/or powders. In certain defined embodiments, oral pharmaceutical compositions will comprise an inert diluent and/or assimilable edible carrier, and/or they may be enclosed in hard and/or soft shell gelatin capsule, and/or they may be compressed into tablets, and/or they may be incorporated directly with the food of the diet. For oral therapeutic administration, the active compounds may be incorporated with excipients and/or used in the form of ingestible tablets, buccal tables, troches, capsules, elixirs, suspensions, syrups, wafers, and/or the like. Such compositions and/or preparations should contain at least 0.1% of active compound. The percentage of the compositions and/or preparations may, of course, be varied and/or may conveniently be between about 2 to about 75% of the weight of the unit, and/or preferably between 25-60%. The amount of active compounds in such therapeutically useful compositions is such that a suitable dosage will be obtained.

The tablets, troches, pills, capsules and/or the like may also contain the following: a binder, as gum tragacanth, acacia, cornstarch, and/or gelatin; excipients, such as dicalcium phosphate; a disintegrating agent, such as corn starch, potato starch, alginic acid and/or the like; a lubricant, such as magnesium stearate; and/or a sweetening agent, such as sucrose, lactose and/or saccharin may be added and/or a flavoring agent, such as peppermint, oil of wintergreen, and/or cherry flavoring. When the dosage unit form is a capsule, it may contain, in addition to materials of the above type, a liquid carrier. Various other materials may be present as coatings and/or to otherwise modify the physical form of the dosage unit.

In certain embodiments of the present invention, the use of lipid formulations and/or nanocapsules is contemplated for the introduction of the compounds of the present invention or pharmaceutically acceptable salts thereof into host cells. Lipid formulations and nanocapsules may be prepared by methods well known in the art.

"Liposome" is a generic term encompassing a variety of single and multilamellar lipid vehicles formed by the generation of enclosed lipid bilayers or aggregates. Liposomes may be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). However, the present invention also encompasses compositions that have different structures in solution than the normal vesicular structure. For example, the lipids may assume a micellar structure or merely exist as nonuniform aggregates of lipid molecules.

Liposomes within the scope of the present invention can be prepared in accordance with known laboratory techniques. In one preferred embodiment, liposomes are prepared by mixing liposomal lipids, in a solvent in a container, e.g., a glass, pear-shaped flask. The container should have a volume ten-times greater than the volume of the expected suspension of liposomes. Using a rotary evaporator, the solvent is removed at approximately 40° C. under negative pressure. The solvent normally is removed within about 5 min. to 2 hours, depending on the desired volume of the liposomes. The composition can be dried further in a desiccator under vacuum. The dried lipids generally are discarded after about 1 week because of a tendency to deteriorate with time.

In the alternative, liposomes can be prepared in accordance with other known laboratory procedures: the method of Bangham et al. (1965), the contents of which are incorporated herein by reference; the method of Gregoriadis, as described in DRUG CARRIERS IN BIOLOGY AND MEDICINE, G. Gregoriadis ed. (1979) pp. 287-341, the contents of which are incorporated herein by reference; the method of Deamer and Uster (1983), the contents of which are incorporated by reference; and the reverse-phase evaporation method as described by Szoka and Papahadjopoulos (1978). The aforementioned methods differ in their respective abilities to entrap aqueous material and their respective aqueous space-to-lipid ratios.

A physiological composition comprising the liposomes will usually include a sterile, pharmaceutically acceptable carrier or diluent, such as water or saline solution.

The present invention also provides kits comprising the compounds of the present invention or physiologically acceptable salts thereof. Such kits will generally contain, in suitable container means, an acceptable formulation of the compounds of the present invention in a physiologically acceptable formulation.

In order to increase the effectiveness of the compounds of the present invention, it may be desirable to combine these compositions with other agents effective in the treatment of hyperproliferative disease, such as anti-cancer agents. An "anti-cancer" agent is capable of negatively affecting cancer in a subject, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer. More generally, these other compositions would be provided in a combined amount effective to kill or inhibit proliferation of the cell. This process may involve contacting the cells with the compounds of the present invention and other agent(s) at the same time. This may be achieved by contacting the cell with a single composition or pharmacological formulation that includes both agents, or by contacting the cell with two distinct compositions or formulations, at the same or different time, wherein one composition includes the compound and the other includes the second agent(s).

Cancer therapies may include a variety of combination therapies with both chemical and radiation based treatments. Combination chemotherapies may include, for example, macrocylic lactones, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, farnesyl-protein tansferase inhibitors, transplatinum, 5-fluorouracil, vincristin, vinblastin and methotrexate, or any analog or derivative variant of the foregoing.

The compounds may also be used together with immunotherapy. Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

In yet another embodiment, the compounds of the present invention may be combined with gene therapy in which a therapeutic polynucleotide is administered before, after, or at the same time as the compound of the present invention. Delivery of a vector encoding one of the following gene products will have a combined anti-hyperproliferative effect on target tissues. In the following sections, genes which can be used in gene therapy in conjunction with administration of the compounds will be described. For example, the compounds may be administered together with an expression construct comprising a tumor suppressor gene, such as, but not limited to, the p53 and p16 gene.

Other genes that may be employed according to the present invention include Rb, APC, DCC, NF-1, NF-2, WT-1, MEN-I, MEN-II, zac1, p73, VHL, MMAC1/PTEN, DBCCR-1, FCC, rsk-3, p27, p27/p16 fusions, p21/p27 fusions, anti-thrombotic genes (e.g., COX-1, TFPI), PGS, Dp, E2F, ras, myc, neu, raf, erb, fms, trk, ret, gsp, hst, abl, E1A, p300, genes involved in angiogenesis (e.g., VEGF, FGF, thrombospondin, BAI-1, GDAIF, or their receptors) and MCC, the Bcl-2 protein family genes, and ICE-like protease genes.

Furthermore, the compounds of the present invention may be used in combination with surgery.

It is contemplated that other agents may be used in combination with the present invention to improve the therapeutic efficacy of treatment. These additional agents include immunomodulatory agents, agents that affect the upregulation of cell surface receptors and GAP junctions, cytostatic and differentiation agents, inhibitors of cell adhesion, or agents that increase the sensitivity of the hyperproliferative cells to apoptotic inducers. Immunomodulatory agents include tumor necrosis factor; interferon alpha, beta, and gamma; IL-2 and other cytokines; F42K and other cytokine analogs; or MIP-1, MIP-1beta, MCP-1, RANTES, and other chemokines. It is further contemplated that the upregulation of cell surface receptors or their ligands such as Fas/Fas ligand, DR4 or DR5/TRAIL would potentiate the chemotherapeutic abilities of the present invention by establishment of an autocrine or paracrine effect on hyperproliferative cells. Increases intercellular signaling by elevating the number of GAP junctions would increase the anti-hyperproliferative effects on the neighboring hyperproliferative cell population. In other embodiments, cytostatic or differentiation agents can be used in combination with the present invention to improve the anti-hyperproliferative efficacy of the treatments. Inhibitors of cell adhesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the present invention to improve the treatment efficacy.

Hormonal therapy may also be used in conjunction with the present invention or in combination with any other cancer therapy previously described. The use of hormones may be employed in the treatment of certain cancers such as breast, prostate, ovarian, or cervical cancer to lower the level or block the effects of certain hormones such as testosterone or estrogen. This treatment is often used in combination with at least one other cancer therapy as a treatment option or to reduce the risk of metastases.

The invention is further illustrated by the following specific examples which are not intended in any way to limit the scope of the invention.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

Synthesis of JL-9 (Formula (III))

FIG. 2 shows a generic scheme for diazonamide synthesis of JL-9. The macrolactam harboring the central core will be built first. This begins by treating dibutyzirconacene 8 with α-chlorostyrene 6 at a −78° C. for three hours (FIG. 4). The region defined vinyl $Zr^{IV}$ species 8 putatively generated in situ is coupled with bromide 5 (FIG. 3) in a process catalyzed by palladium to afford a 1,1-disubstituted ethylene 9. This is the application of Takahashi's modification of a Negishi coupling neither requires nor benefits from a Zr to Zn transmetalation prior to addition of the electrophile. The protecting groups on 9 are subsequently removed by allowing the reaction mixture to come to room temperature for 1.5 hours to generate phenol 10. 10 is condensed with tyrosine derivative 4 in the presence of DMF and diisopropylamine to afford modified dipeptide 11.

Referring to FIG. 5, 11 is exposed to catalytic $Pd^0$ in the presence of $Ag_3PO_4$ at 75° C. for eight hours to produce lactam 13. This pivotal Heck endocyclization is novel in that success appears due to formation of a cyclic $Pd^{II}$ phenoxide (for example, 12 L=2-(di-tert-butylphosphino)biphenyl) prior to carbometalation of the vinylogous acrylonitrile within the catalytic cycle.

Compound 13 has the content of a diazonamide core and needs only to be oxidatively restructured. After the E-ring phenol is derivatized as its 2-bromoethyl ether, oxidation is achieved by exposure to the complex formed between $OsO_4$ and (1S,2S)-N,N'-bis(3,3-dimethylbutyl)-cyclohexane-1,2-diamine (14). Decomposition of the incipient $Os^{VI}$ glycolates with $H_2S$ provides a 93:7 ratio of diasteromeric syn—glycols favoring 15—a particularly gratifying outcome for this stereochemically mis-matched construction. This reaction occurs at −50° C. for four hours. With 15 in hand, its restructuring takes the form of a ring-contracting pinacol rearrangement initiated with dry p-TsOH (FIG. 5) incubated at 95° C. for 40 minutes. The p-TsOH is added in three equal portions at ten minute intervals during the first thirty minutes of the reaction. While efficiency is modest for change, stereochemical communication is near perfect, presumably mediated by phenonium ion 16, as triarylacetaldehyde 17 is produced as a single C10 isomer at room temperature. It should be mentioned that the operations converting 13 to 17 are the only deliberate stereochemical manipulations. The axial asymmetries of the diazonamide polycycle can now be made an artifact of their assembly.

Alterations of compound 15 are necessary to prepare for incorporation of this additional diazonamide structure (FIG. 5). Following carbamoylation of the C2 amine, reduction of the C10 aldehyde, and degradation of the 2-bromoethyl ether, the resultant E-ring phenol is selectively ortho-brominated to afford 18. The difference in acidity of free nucleophiles present in 18 allows selective re-etherification of the phenol. This product is then exposed to moist $Cl_3CCO_2H$ to provide lactone 19 via intramolecular alkoxylation of the C29 nitrile and in situ hydrolysis of the formed imidate.

An indole segment can be incorporated into structures of type 19 via lactone opening with the dimethlyaluminum amide derived from tryptamine. The product of this reaction is then oxidized with catalytic TPAP and stoichiometric NMO to afford 20. Alternatively, a three step sequence, with an altered timing of events is therefore used to achieve the intended result (19→20) (FIG. 6). Brief photolysis (350 nm) of 20 in dilute dioxane solution then provides a crude C11 hemiacetal that is acylated with $Ac_2O$ to afford a single diastereomer of acetate 21. Established techniques parlay the β-keto amide segment of this compound into oxazole 22 and position us for completion of diazonamide polycycle.

Irradiation of degassed solutions of 22 (300 nm-Rayonet, $5\times10^{-3}$ M in 3:1 $CH_3CN/H_2O$) results in loss of HBr and formation of internal arylation product 24. A single regioisomeric biaryl (a-single atropdiastereomer) is isolated from this reaction although there is competing production of uncyclized materials lacking bromine. One interpretation of this Witkop-type cyclization involves intramolecular photo-induced electron transfer from the indole ring to the adjacent bromo arene. Mesolytic elimination of bromide from the resultant radical ion pair 23, biradical collapse, and prototrophy in first formed 4H-indole 24 would give 25. The benefit realized by including Li+ ions into the medium, the inability of 4-methyl-2,6-di(tert-butyl)phenol to inhibit the reaction, and the observation that materials chlorinated at C25 and C27 do not photocyclize similarly are consistent with this simple view.

Figure 8:
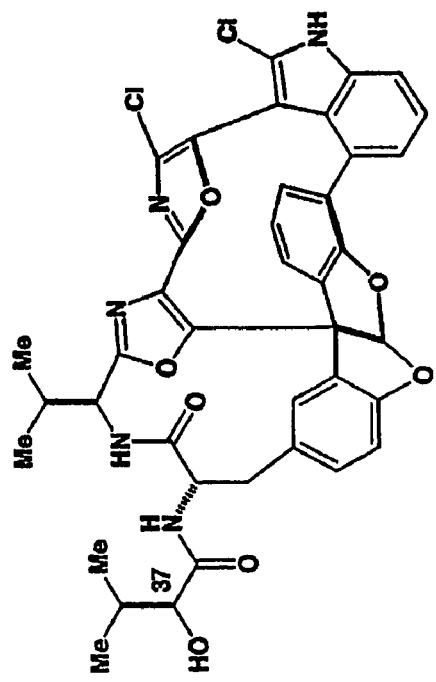
FIG. 8 shows the structure of synthesized diazonamide compounds, JL-9 and JL-10.
Figure 8:
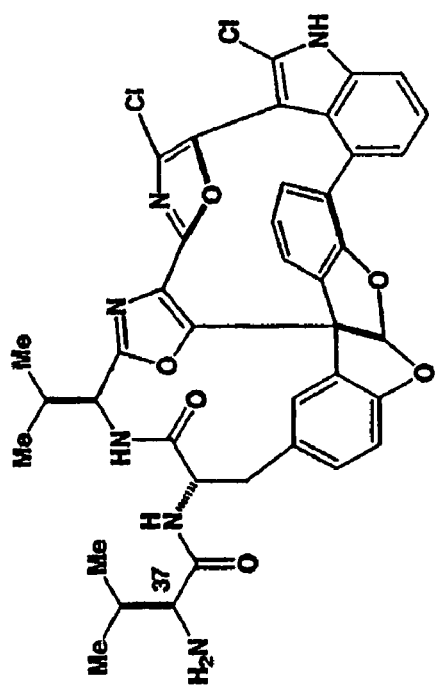

To complete the synthesis, compound 25 is chlorinated with N-chlorosuccinimide and treated with Amberlyst-15 acidic resin to initiate dealkylative C11 acetal formation (FIG. 7). The benzyl carbamate of the product formed (27) is hydrogenolyzed and the free amine produced acylated with L-α-hydroxy isovaleric acid using diethylphosphoryl cyanide to provide JL-9 28, the compound of formula (III) (FIG. 8).

Nuclear magnetic resonance (NMR) spectra were recorded on either a Varian Inova-400 or Mercury-300 magnetic resonance spectrometer. $^1H$ NMR chemical shifts are given in parts-per-million (δ) downfield from tetramethylsilane using the residual solvent signal ($CHCl_3$=δ 7.27, acetone=δ 2.05, methanol=δ 4.87, tetrahydrofuran=δ 1.73) as internal standard. $^1H$ NMR information is tabulated in the following format: number of protons, multiplicity (s, singlet; d, doublet; t, triplet; q, quartet; m, multiplet, td, triplet of doublet; dt, doublet of triplet), coupling constant(s) (J) in hertz. The prefix app is occasionally applied in cases where the true signal multiplicity was unresolved and br indicates a broad signal.

JL-9 28: $^1H$ NMR (400 MHz, $CD_3OD$, 25° C.): δ=7.50 (d, J=2.0 Hz, 1H), 7.46 (dd, J=8.4, 0.8 Hz, 1H), 7.36 (appt, J=7.6 Hz, 1H), 7.26 (dd, J=8.4, 2.0 Hz, 1H), 7.21-7.19 (m, 2H), 7.07 (dd, J=7.6, 1.2 Hz, 1H), 6.93 (appt, J=7.6 Hz, 1H), 6.88 (d, J=8.0 Hz, 1H), 6.84 (s, 1H), 4.97 (d, J=6.0 Hz, 1H), 4.61 (dd, J=11.6, 3.2 Hz, 1H), 3.89 (d, J=4.0 Hz, 1H), 3.46 (t, J=12.4 Hz, 1H), 2.80 (dd, J=12.8, 3.2 Hz, 1H), 2.32-2.27 (m, 1H), 2.14-2.09 (m, 1H), 1.09 (d, J=6.8 Hz, 3H), 1.02 (d, J=6.8 Hz, 3H), 0.96 (d, J=6.8 Hz, 3H), 0.92 (d, J=6.8 Hz, 3H). ES-MS: calcd for $C_{40}H_{33}Cl_2N_5O_7$ [M+H]$^+$: 766.19, found: 766.30; calcd for $C_{40}H_{33}Cl_2N_5O_7$ [M−H]$^-$: 764.17, found: 764.31; LR-MS (FAB) calcd for $C_{40}H_{33}Cl_2N_5O_7$ [M+H]$^+$: 766.19, found: 766.35.

2: $R_f$=0.72 (35% EtOAc/benzene); $[\alpha]_D^{25}$=−108.8° (c=0.32, MeOH); IR (film): v=3281, 2965, 1660, 1651, 1644, 1538, 1479, 1063, 752 cm$^{-1}$; 1H NMR (400 MHz, [$D_4$] MeOH, 25° C.): δ=7.79 (d, J=8.4 Hz, 2H), 7.66 (d, J=8.4 Hz, 2H), 7.52 (s, 1H), 751 (s, 1H), 7.48 (dd, J=0.8, 8.4 Hz, 1H), 7.38 (app t, J=8.4 Hz, 1H), 7.24 (m, 2H), 7.11 (dd,J=1.2, 7.6 Hz, 1H), 6.97 (appt, J=7.6 Hz, 1H), 6.93 (s, 1H), 4.99 (d, J=6.0 Hz, 1H), 4.76 (dd, J=2.8, 12.0 Hz, 1H), 3.60 (app t, J=12.0 Hz, 1H), 2.92 (dd, J=3.2, 12.8 Hz, 1 H), 2.36-2.28 (sym 6-line m, 1H), 1.11 (d, J=6.8 Hz, 3H), 1.01 (d, J=6.8 Hz, 3 H); $^{13}C$ NMR (75 MHz, [$D_4$]MeOH, 25° C.): δ=174.9, 168.6, 163.4, 159.7, 156.5, 154.8, 152.9, 141.9, 139.9, 136.7, 134.5, 134.4, 133.6, 133.0, 132.7, 130.7, 130.6, 130.6, 130.2, 129.6, 129.2, 128.8, 127.5, 126.4, 125.4, 124.5, 124.17, 124.16, 122.7, 119.5, 112.5, 104.0, 98.0, 63.1, 58.4, 56.6, 37.9, 31.6, 19.5, 18.8; ES-MS: calcd for $C_{42}H_{27}Br_2Cl_2N_5O_6$ [M$^+$+H]: 925.98, found: 926.04; calcd for $C_{42}H_{27}Br_2Cl_2N_5O_6$ [M−−H]: 923.96, found: 923.96; HR-FAB-MS: calcd for $C_{42}H_{27}Br_2Cl_2N_5O_6$[M++Li]: 931.9865, found: 931.9878.

26: $R_f$=0.25 (50% EtOAc/benzene); $[\alpha]_D^{25}$=−211.80° (c=O.40,MeOH);IR (film): v=3270, 2966, 1766, 1658, 1651, 1514, 1205, 1048, 754 cm$^{-1}$ $^1H$ NMR (400 MHz, [$D_4$]MeOH, 25° C.): δ=8.75 (s, 1H), 7.43 (d, J=8.0 Hz, 1H) 7.38-7.30 (m, 6H), 7.15 (d, J=7.6 Hz, 1H), 7.10 (d, J=7.6 Hz, 1H), 6.84-6.75 (m, 4H), 6.54 (d, J=1.2 Hz, 1H), 5.11 (s, 2H), 4.50 (dd, J=2.4, 11.2 Hz, 1H), 4.47 (d, J=8.8 Hz, 1 H), 3.97 (d, J=6.8 Hz, 1H), 3.22 (app t, J=12.8 Hz, 1H), 2.66 (dd, J=2.4, 12.8 Hz, 1H), 2.08-1.98 (m, 2H), 1.84 (s, 3H), 1.07 (d, J=6.4 Hz, 3H), 0.96-0.93 (m, 9H); $^{13}C$ NMR (75 MHz, [$D_4$]MeOH, 25° C.): δ=173.5, 172.3, 169.0, 163.8, 157.4, 156.5, 154.1, 154.0, 153.8, 140.9, 137.0, 135.3, 133.5, 132.2, 130.0, 129.1, 128.3, 127.9, 127.8, 127.8, 127.7, 127.1, 126.5, 126.3, 126.0, 124.2, 123.4, 122.8, 122.7, 121.6, 121.3, 117.1, 110.8, 100.7, 97.5, 66.5, 60.7, 59.2, 56.7, 55.2, 37.0, 31.1, 30.2, 19.4, 19.1, 18.4, 18.2, 17.5; ES-MS: calcd for $C_{50}H_{44}Cl_2N_6O_{10}$ [M++H]: 959.26, found: 959.25; calcd for $C_{50}H_{44}Cl_2N_6O_{10}$ [M−−H] 957.24, found: 957.26.

Example 2

Comparison of JL-9 and Original Diazonamide Structure

Characteristics of synthesized diazonamide compound, JL-9, were compared to naturally occurring diazonamide. JL-9 was susceptible to handling and its mobility on thin-layer chromatography differed from naturally occurring diazonamide A. Li et al. Angew Chem Int Ed, 2001, 40:4765-4769. Mass spectrometry indicates that late synthetic intermediates begin to decompose through net C10 deformylation almost immediately after unmasking a free C11 hemiacetal. The process completes upon attempted preparative HPLC purification of 1b (FIG. 1) under conditions identical to those used to isolate natural (−)-diazonamide A. In addition, a second degradation pathway available in this series appears as a result of the cleavage of the strained macrolactam ring through diketopiperazine formation that involves the C37 amine and the C12 amide carbonyl. This suggested a misassignment of the C2 amine appendage.

Spectroscopic data for the heterocyclic cores of diazonamides A and B are nearly identical. So when the crystal structure of a p-bromobenzamide derivative of diazonamide B 2 was reported, the diazonamide A assignment seemed only to require reconciling its exact mass (765.1.998 amu) within the same framework. The high resolution FAB mass spectrum of diazonamide A shows a cluster of six ions between 765 and 770 amu, the relative intensity of which indicates the presence of two chlorine atoms. Heavy-atom analysis confirms that chlorine is the only halogen present. The molecular formula $C_{40}H_{35}N_6O_6Cl_2$ is consistent with this mass (Δ−0.3 ppm) although it was thought to reflect a desiccated form of the molecule as a result of a C11 hemiacetal that loses water during HRMS analysis. Likewise, the C11 diphenylacetal reported in 2 (see FIG. 1) was thought a result of net dehydration occurring during derivatization of diazonamide B with p-bromobenzoyl chloride. Hemiacetal functionality was considered a necessary part of both natural products to accommodate a small vicinal coupling between C11H and an exchangeable, one-proton resonance just over δ=7 in $^1H$ NMR spectra ([$D_6$]DMSO). The diazonamide A assignment 1 b (FIG. 1) was then completed by incorporation of a terminal valine residue which emanates from the C2 amine. In the context of a C11 hemiacetal, this designation does coincide with the high resolution mass measurement but, unfortunately, with little else.

Acid digests of diazonamide A do not produce valine. Lindquist, N., PhD thesis, University of California San Diego, 1989. $^1$H NMR (360 MHz, ([D$_6$]DMSO) indicates the presence of two isopropyl groups in the molecule, but the N7 protons are reported as a sharp, one-proton doublet at δ=5.46. This resonance is, in turn, coupled (5.9 Hz) to the C37 methine hydrogen at δ=3.75. The corresponding C37 methine resonance in synthetic diazonamide 1*b* appears at δ=3.2 (400 MHz, [D$_6$]DMSO) and is broadened. In a triacetate derivative, the C37 proton shifts downfield to δ=5.11, although it now appears as a doublet rather than the more complex pattern one might expect for a C37 acetamide. Peracetylated diazonamide A shows three methyl singlets at δ=2.87, 2.23, 2.16 in its $^1$H NMR spectrum (360 MHz, CDCl$_3$) and two new IR absorbances at 1760 cm$^{-1}$ and 1725 cm$^{-1}$. Moreover, in non-acetylated material, C37 resonates at δ=76.9 (50 MHz, [D4]MeOH), which is considerably downfield from the corresponding carbon atom in a typical valine free-base. As a result, these observations are consistent with the view that the C37 substituent in natural diazonamide A is an alcohol rather than an amine.

For this to be true, the NH$_2$ to OH change dictates that a compensatory permutation be made at another position in the structure to rectify the attendant increase by 1 Da in molecular mass. This requires revising the X-ray structure assigned as 2. Notably, the exact mass of diazonamide B is 743.0340 amu. However, the structure proposed for this material 2 has the formula C$_{40}$H$_{26}$N$_5$O$_6$Cl$_2$Br and an [M$^+$+H] —H2O] ion has the calculated mass 744.0416 amu. The formula C$_{40}$H$_{25}$N$_6$O$_4$Cl$_2$Br [M$^+$+H]=743.0576 amu] is more consistent with the observed mass (Δ=2.4 ppm) and this suggests that a protonated nitrogen atom in diazonamide B has been mistaken for oxygen in 2 (see FIG. 1).

C11 hemiacetals in natural diazonamides are not indicated by mass spectrometry. Moreover, synthetic materials with this functional group (namely, 1*b*) ionize intact, which makes the O2 or O3 assignment suspect. In the structure assigned as 2, the observed C7-O2 bond length (1.371 Å) falls within the range typical for aryl C—O bond distances (1.353-1.409 Å) and deviates by just 1.5σ (σ=standard deviation) from the mean value of 1.385 Å (based upon 36 bonds in 20 related substructures found within the Cambridge Crystallographic Database). However, the C17-O3 bond, likewise expected to be an aryl C—O bond, is measured at 1.433(16) Å. This is 0.048 Å (3σ) longer than the mean and, notably, exceeds the maximal value (1.409 Å) observed for a bond of this type. Atom O3 also displays an unusually large thermal motion for an atom in a rigid group (FIG. 1). The average B-factor (B$_{eq}$) in the core (O3 excluded) is 4.8(3) Å$^2$ while the temperature factor of O3 itself is 7.42 Å$^2$, or 8.7σ above the average. This is in comparison to O2 and O3 in the X-ray structure refinement of synthetic diphenyl acetal 28, which are Beq=6.00 and 5.35 Å$^2$, respectively. (see FIG. 7) This indicates that the O3 assignment should be changed to an element with fewer electrons and a larger covalent radius.

Figure 9:
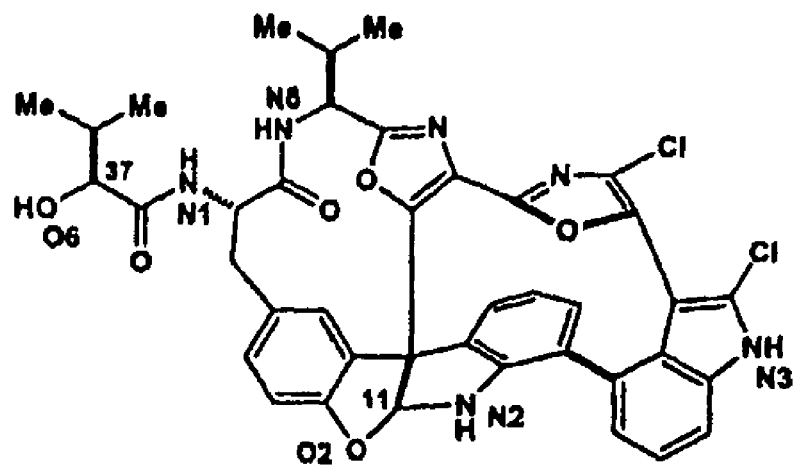
FIG. 9 shows the revised structures of diazonamide A and B.
Figure 9:
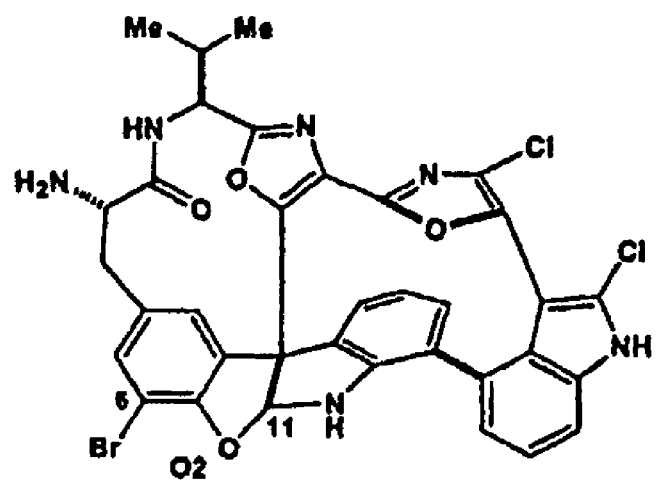

When taken together, these data are consistent with the electron density assigned as O3 being a protonated nitrogen atom and, by extension, the actual structure of (−)-diazonamide B being C11 diarylaminal 31 (FIG. 9). This change, in combination with an S-configured C37 alcohol, gives 30 as our revised structure of (−)-diazonamide A. $^1$H NMR spectra of 28 (JL-9) and its C37 epimer (derived from D-α-hydroxy isovaleric acid) are near identical. C37-S stereochemistry in 30 is based upon relative potencies in cell-based assays. (See Table 2).

Figure 10:
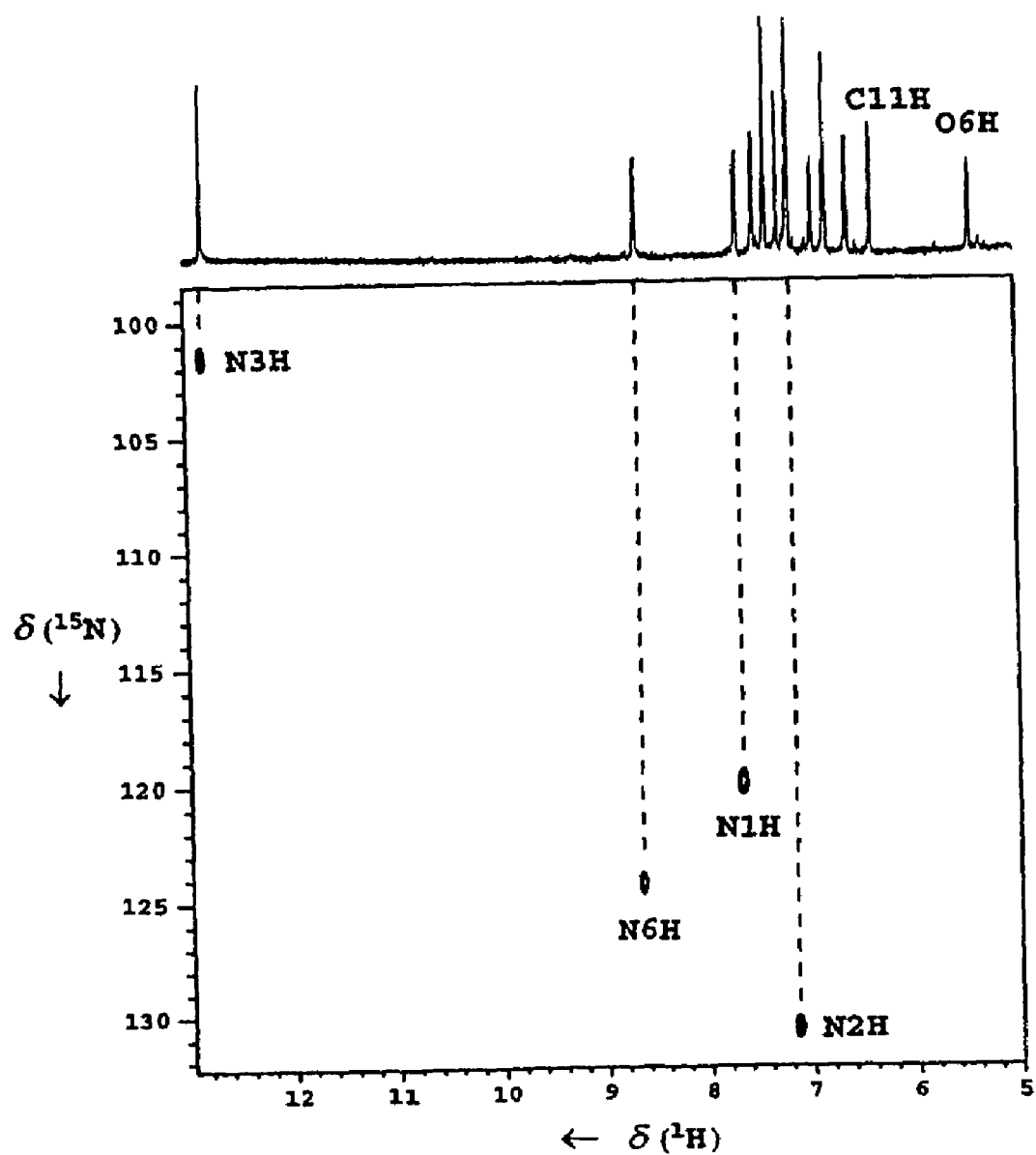
FIG. 10 shows a partial $^1H/^{15}N$-HSQC spectrum of natural diazonamide.

An $^1$H/$^{15}$N-HSQC experiment on natural diazonamide A was performed to support this assignment (FIG. 10). The $^1$H/$^{15}$N-HSQC experiment allows protons attached to nitrogen to be uniquely identified. Kay et al. J Am Chem Soc, 1992, 114:10663-10665. The $^1$H/$^{15}$N-HSQC, $^1$H/$^{13}$C-HSQC, and DQF-COSY experiments were recorded at 25° C. on a 500 MHz Varian Inova spectrophotometer.

The two dimensional spectrum shown in FIG. 10 indicated four such connectives in the natural product: δ=12.82 (N3H); δ=8.66 (N6H); δ=7.68 (N1H); δ=7.16 (N2H). The proton resonance at δ=7.16 is coupled to C11H (DQF-COSY) and was originally assigned as O7H in 1*b*. Moreover, the exchangeable one-proton doublet at δ=5.46, first identified as N7H$_2$, is not coupled to $^{15}$N, which is consistent with our C37 hydroxyl model.

The inventors initially considered the possibility that misassignments were made only in the C2 amine side chain. An a-hydroxy amidine congener of 1*b* was prepared. This material incorporates a C37 carbinol and does have the same net atomic composition as 1*b*. However, chromatographic and spectroscopic properties of the compound rule it out as a possibility.

Example 3

Synthesis of Naturally Occuring Diazonamide

Synthesis of compounds of formula (IV) and (V) is disclosed in accordance with the reaction scheme of FIG. 11. In particular, polyamide 32 may be assembled by standard F-Moc-based peptide synthesis beginning with compounds 38-41. Treatment of 32 with excess (4-5 equivalence) DDQ may oxygenate the 2 indole benzylic positions to provide a diaryl ketone. This product then undergoes a double cyclodehydration when exposed to Ph3PBr2 in dichloromethane solvent. Removal of the allyl protecting groups in the bis(oxazoyl)indole product may then provide phenol 33 (FIG. 11). A 2-electron oxidation of 33 using, for example, an iodine (III) reagent initiates a cyclization between an electron-deficient intermediate and the adjacent indole halo sidechain (as indicated) to afford 34. This substance may be photocyclized to a complete diazonamide skeleton 35 in a manner directly analogous to that used in the synthesis of 25 from 22 (see FIG. 6). Chlorination of 35 with n-chlorosuccinimide and cleavage of o-nitrophenylsulphonamide protecting group with a sulfur nucleophile provides 36. This free amine can be acetylated with S-α-hydroisovaleric acid to provide diazonamide A 30.

Example 4

Biosynthetic Origin of Diazonamide Compounds

The aforementioned studies suggest that diazonamide compounds may be biosynthetically constructed from four natural amino acids (FIG. 12). The polyheterocyclic core may be a derivative of an oxidized, 4,7-linked ditryptophan unit with the macrolactam ring being formed by a net oxidative cycloaddition between tyrosine and tryptophan. Although the oxidative cycloaddition has yet to be identified, the produc-

Example 5

Growth Inhibition Activity of Diazonamide Compounds

Figure 13:
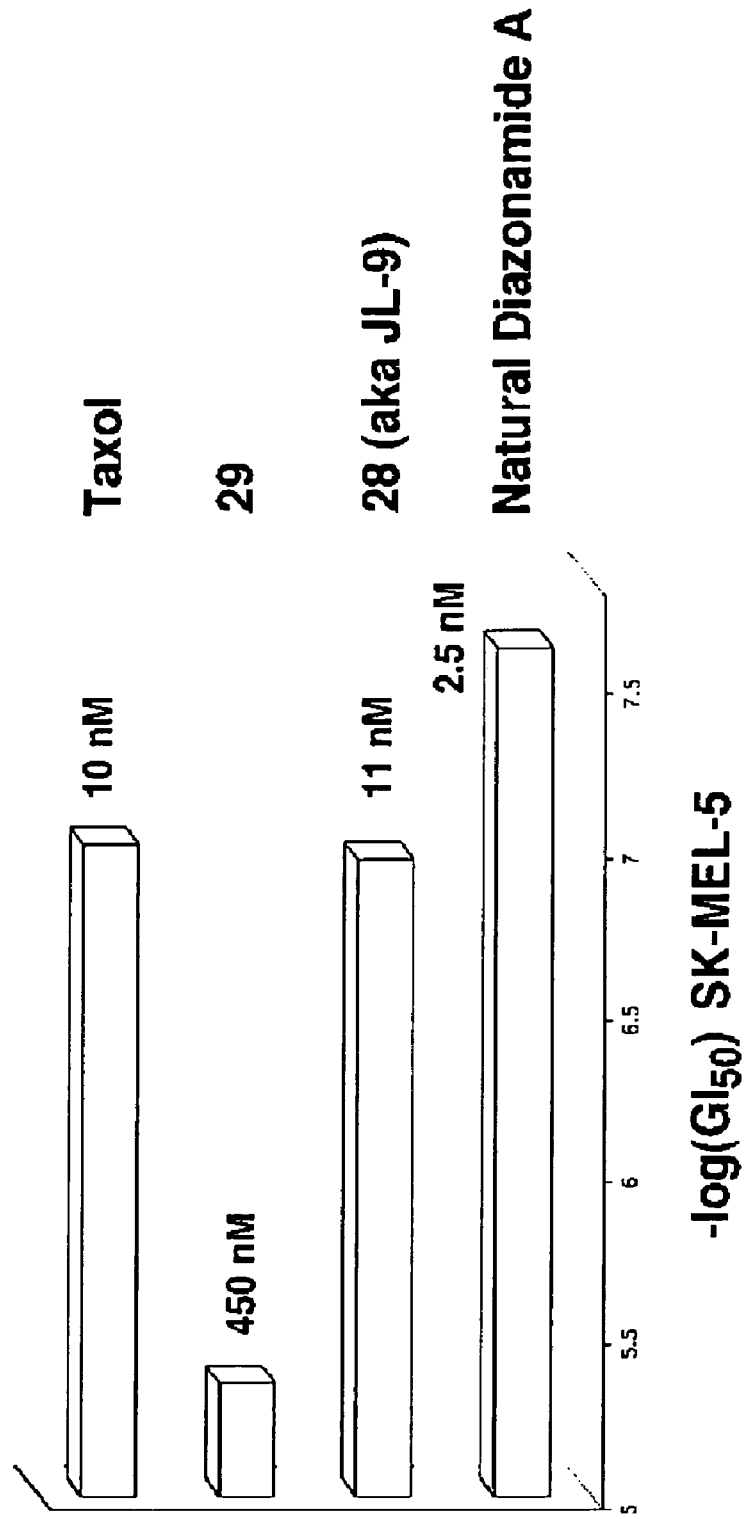
FIG. 13 shows a bar graph comparing cytotoxic effects of JL-9, JL-10 with taxol and naturally occurring diazonamide A on SK-MEL-5 cells.

MTT assays were performed to demonstrate the cytotoxic effect of JL-9 on SK-MEL-5, a human malignant melanoma cell line. This assay measures cellular viability and proliferation based on the ability of live cells to take up and cleave a tetrazolium salt to generate a colored product. FIG. 13 shows that JL-9 has a potent cytotoxic and growth inhibitory effect on SK-MEL-5. JL-9 significantly inhibits cell proliferation in comparison to JL-10, an inactive analogue. Similar results have been obtained with various tumor cell lines, such as HCT-116, a human colorectal carcinoma, OVCAR-3, a human ovarian adenocarcinoma, 786-0, a human renal cell adenocarcinoma, BSC-1, a kidney epithelial cell line from African green monkey, and CHO-K1, a Chinese hamster ovarian epithelial cell line.

A growth inhibition study was also conducted using OVCAR-3 (a human ovarian adenocarcinoma) cells. Human ovarian adenocarcinoma OVCAR-3 cells are treated with diazonamide and control compounds for 48 hours and evaluated for cell viability using the Promega CellTiter-Glo™ Assay (Promega, Madison, Wis.). This assay uses luciferase to measure ATP as indicator of metabolically active cells. The results are shown in Table 2 below.

JL-9 28 is >50-fold more potent than amine JL-10 29 at inhibiting the growth of human ovarian adenocarcinoma OVCAR-3 in vitro, while being equipotent to natural diazonamide A and paclitaxel.

TABLE 2

In Vitro Cytotoxicity Assay

| Compound | GI50 (nM) |
| --- | --- |
| natural diazonamide | 8 |
| JL-9 28 | 16 |
| JL-9 (epi-C37) 28 | 191 |
| JL-10 29 | 845 |
| 2 | >10,000 |
| paclitaxel | 8 |

Example 6

FACS (Fluorescence Activated Cell Sorting) Analysis

FACS Analysis was performed on HCT-116 cells to examine the effect of JL-9 on mitosis. 150,000 HCT-116 cells were incubated per well with media into six well tissue culture plates. Cells were allowed to adhere for 16-18 hours. Media containing 0.01% ethanol (vehicle control), 30 nanomolar (nM) taxol, 30 nM vinblastine and 30 nM JL-9 was added to cells and incubated for 12, 24, 36, or 48 hours. At these time points, cells were harvested with 0.25% trypsin 1 mM EDTA, and transferred to 1.5 ml Eppendorf tubes. Cells were pelleted and washed twice with 1× PBS. Cells were then fixed in –20° C. 100% ethanol and stored at 4° C. Cells were pelleted from 100% ethanol, washed once with 1× PBS, and treated with Vindelov's propidium iodide solution (50 ug/ml propidium iodide, 0.01 mM NaCl, 0.1% IPEGAL, 0.01 mg RNase) and 1 mg/ml RNAse for 30 minutes at 37° C. Propidium iodide is a fluorescent marker that binds to nucleotides. It can be used with FACS scan analysis to determine the ploidy of a population of cells. FACS scan analysis was performed using Beckman-Dickinson FACScan instrument. Data was analyzed using Cell Quest software.

Figure 14:
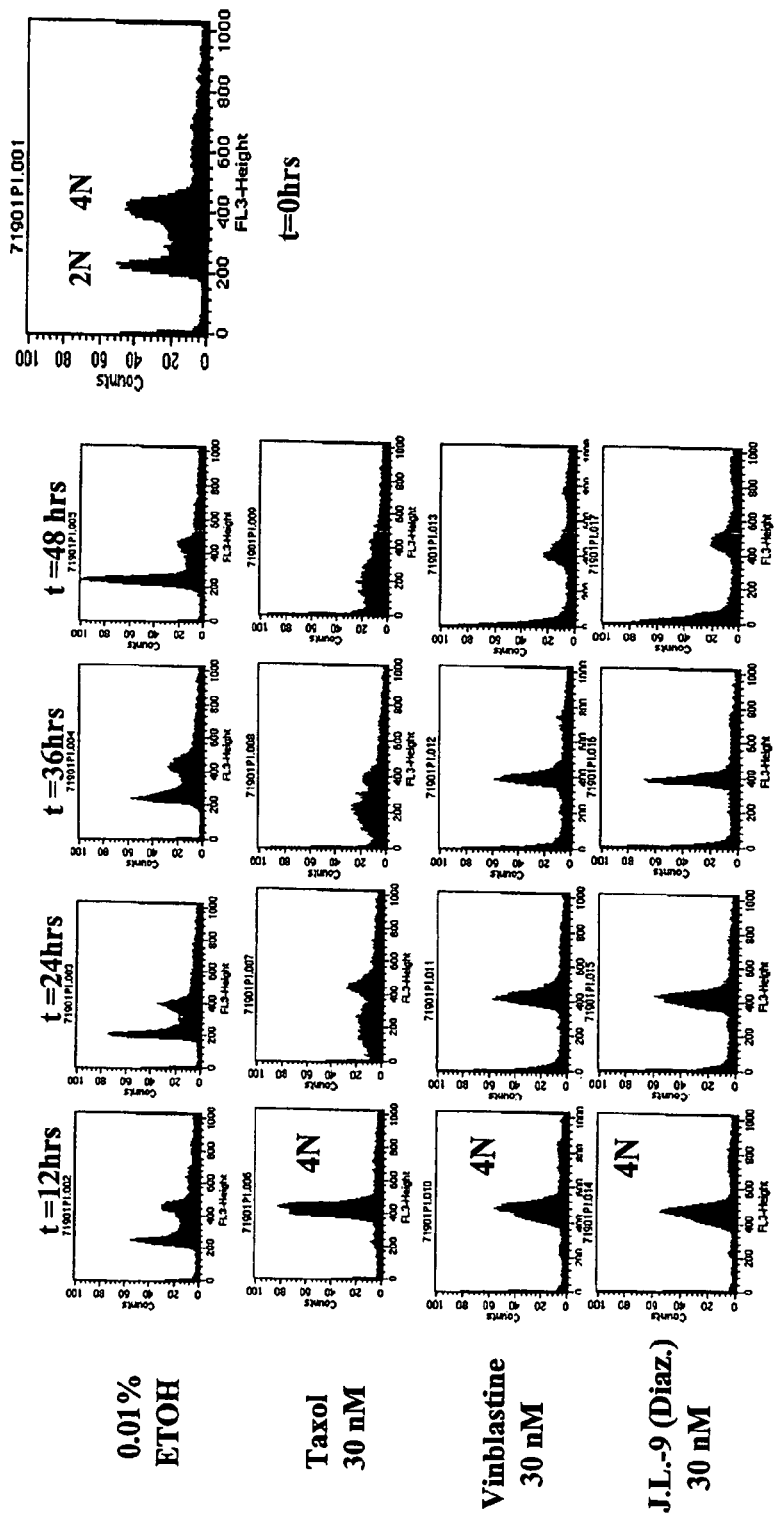
FIG. 14 shows a FACS Scan of HCT-116 cells treated with JL-9, taxol and vinblastine.

FIG. 14 demonstrates that JL-9 arrests HCT-116 cells in the tetraploid (4n) state in a similar fashion to other anti-mitotic agents, taxol, and vinblastine. This is in contrast to control treated samples which exhibit both diploid and tetraploid populations.

Example 7

Determination of Effect of JL-9 on Cellular Tubulin Cytoskeleton Using Indirect Immunofluorescence Immunofluorescence was performed on JL-9, taxol, vinblastine, control-treated OVCAR-3 cells to examine their effects on tubulin cytoskeleton. Cells were grown on 2 cm glass cover slips in tissue culture wells. Media containing JL-9, vinblastine, or taxol was added at various concentrations and incubated for 12 or 23 hours. Hoescht 33343 nuclear dye was added directly to the media (1.5 ug/ml) and incubated at 37° C. for 30 minutes. Coverslips were washed 3× with 1× PBS and fixed for 10 minutes with –20 C 100% methanol. Coverslips were washed 3× with 1× PBS/1% BSA and treated directly with a ½000 dilution of anti-α-tubulin antibody (mouse anti-human). Coverslips were washed 3× with 1× PBS/1% BSA and treated with ⅕00 dilution of fluorescently conjugated goat anti-mouse secondary antibody (Alexa Fluor 488). Coverslips were washed 3× with 1× PBS/1% BSA and mounted on microscope slides using mounting media (Aqua Poly Mount). Images were obtained using Zeiss Axiovert 100M digital light and confocal microscopy. Our data demonstrate that JL-9 treatment creates aberrant effects on the cytoskeleton and formation of abnormal mitotic spindles.

Immunofluorescence was also performed on JL-9, JL-10, taxol and vinblastine-treated BSC-1 cells subjected to thymidine block. BCS-1 African Green Monkey kidney cells were treated for 18 hours in culture medium containing 2 mM thymidine and then returned to normal medium containing 100 nM of taxol, vinblastine, JL-10 (control) or JL-9 for 12 hours. During the last 30 minutes, Hoecht's dye was added to 100 nM to stain chromosomes. Cells were fixed in cold methanol and stained with antibody specific for alpha tubulin. Images of the organization of microtubules in spindles were collected with a laser scanning confocal microscope using a single 488 nm excitation wavelength.

Mitotic figures were frequently found in samples treated with JL-9, taxol or vinblastine. None of the cells are able to construct normal bipolar mitotic spindles. This is in contrast to cells treated with JL-10, which resembled the vehicle controls.

The present invention is not to be limited in scope by the specific embodiments described herein. Indeed, various modifications of the invention in addition to those described herein will become apparent to those skilled in the art from the foregoing description and accompanying Figures. Such modifications are intended to fall within the scope of the appended claims. Various references are cited herein, the disclosure of which are incorporated by reference in their entireties.

We claim:
1. A compound having the formula (I):

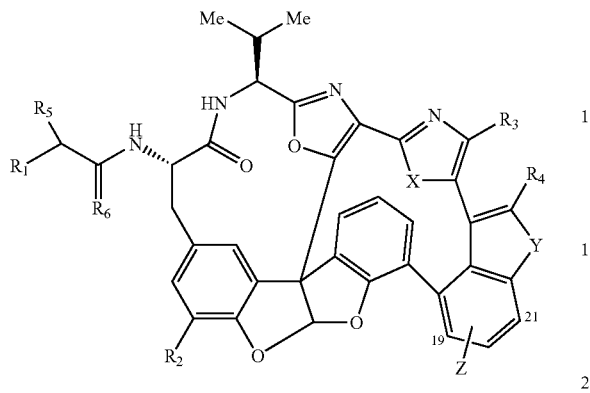

wherein
R₁ is OR₇, or NHR₇;
R₂ is H, Cl, Br, or I;
R₃ is H, Br, I, phenyl, ethynyl, straight chain saturated alkyl, or straight chain unsaturated alkyl;
R₄ is H, Br, I, phenyl, ethynyl, straight chain saturated alkyl, or straight chain unsaturated alkyl;
R₅ is H, straight chain saturated alkyl, straight chain unsaturated alkyl, branched chain saturated alkyl, branched chain unsaturated alkyl, aryl, or substituted aryl;
R₆ is O, NH, or S;
X is O or S;
Y is O, or NR₈;
Z is H, 19-OH, or 21-OR₈;
R₇ is H, straight chain saturated alkyl, straight chain unsaturated alkyl, acyl or aryl; and
R₈ is H, straight chain saturated alkyl, straight chain unsaturated alkyl, acyl, or aryl.

2. A compound having the formula (II):

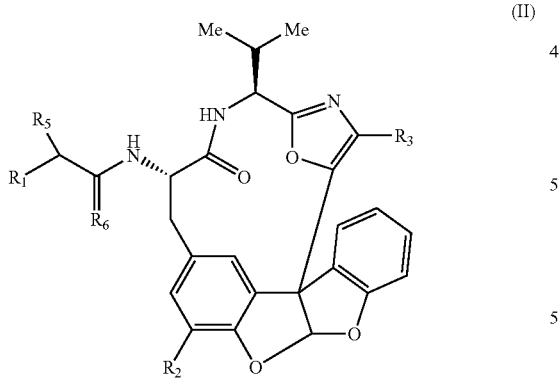

wherein
R₁ is OR₇, or NHR₇;
R₂ is H, Cl, Br, or I;
R₃ is H, CN, or CO₂R₉;
R₅ is H, straight chain saturated alkyl, straight chain unsaturated alkyl, branched saturated chain alkyl, branched chain unsaturated alkyl, aryl, or substituted aryl;
R₆ is O, NH, or S;

R₇ is H, straight chain saturated alkyl, straight chain unsaturated alkyl, acyl, aryl, or aryl; and
R₉ is H, aryl, benzyl, allyl, straight chain saturated alkyl, straight chain unsaturated alkyl, branched saturated chain alkyl, or branched chain unsaturated alkyl.

3. A compound having the formula (V):

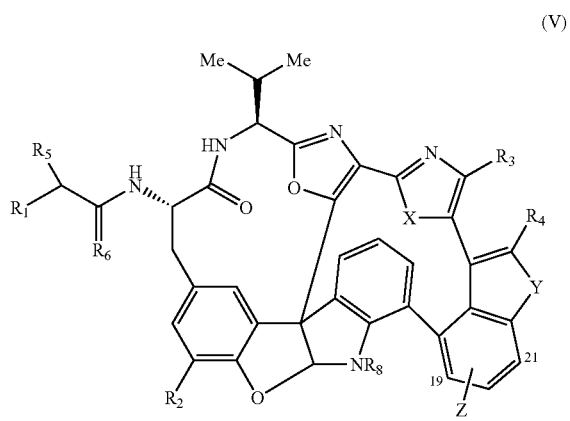

wherein the compound is a synthetic variant of *Diazona angulata* diazonamide A or B (structure 30 and 31, respectively),

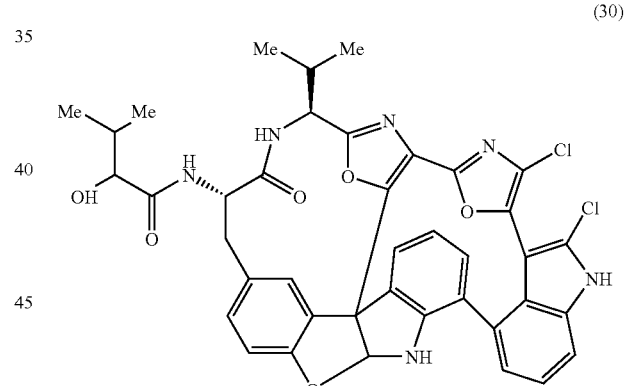

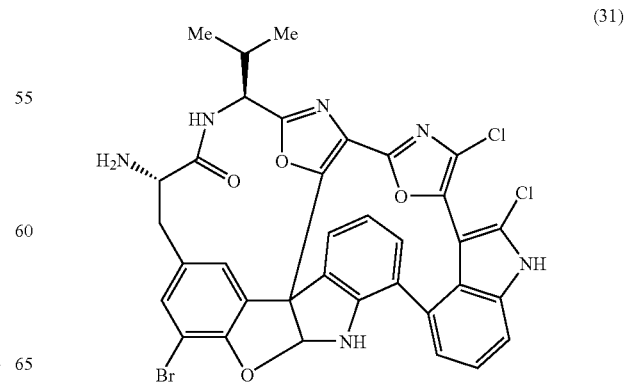

and wherein
$R_1$ is $OR_7$, or $NHR_7$;
$R_2$ is H, Cl, Br, or I;
$R_3$ is H, Cl, Br, I, phenyl, ethynyl, straight chain saturated alkyl, or straight chain unsaturated alkyl;
$R_4$ is H, Cl, Br, I, phenyl, ethynyl, straight chain saturated alkyl, or straight chain unsaturated alkyl;
$R_5$ is H, straight chain saturated alkyl, straight chain unsaturated alkyl, branched chain saturated alkyl, branched chain unsaturated alkyl, aryl, or substituted aryl;
$R_6$ is O, NH, or S;
X is O or S;
Y is O, or $NR_8$;
Z is H, 19-OH, or 21-$OR_8$;
$R_7$ is H, straight chain saturated alkyl, straight chain unsaturated alkyl, acyl, aryl, or aryl; and
$R_8$ is H, straight chain saturated alkyl, straight chain unsaturated alkyl, acyl, or aryl;
wherein said compound of formula V cannot be of formula 30 or 31.

4. A compound having the formula (VI):

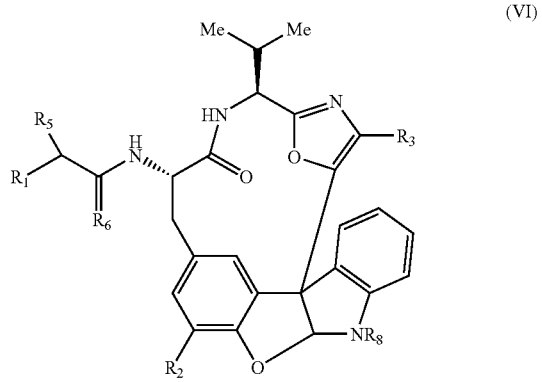

wherein
$R_1$ is $OR_7$, or $NHR_7$;
$R_2$ is H, Cl, Br, or I;
$R_3$ is H, CN, or $CO_2R_9$;
$R_5$ is H, straight chain saturated alkyl, straight chain unsaturated alkyl, branched saturated chain alkyl, or branched chain unsaturated alkyl, aryl, or substituted aryl;
$R_6$ is O, NH, or S;
$R_7$ is H, straight chain saturated alkyl, straight chain unsaturated alkyl, acyl or aryl;
$R_8$ is H, straight chain saturated alkyl, straight chain unsaturated alkyl, acyl, or aryl; and
$R_9$ is H, aryl, benzyl, allyl, straight chain saturated alkyl, straight chain unsaturated alkyl, branched saturated chain alkyl, or branched chain unsaturated alkyl.

5. The compound of claim 3, wherein
$R_1$ is $OR_7$, or $NHR_7$;
$R_2$ is H, Cl, Br, or I;
$R_3$ is H, Cl, Br, I, phenyl, ethynyl, straight chain saturated alkyl, or straight chain unsaturated alkyl;
$R_4$ is H, Cl, Br, I, phenyl, ethynyl, straight chain saturated alkyl, or straight chain unsaturated alkyl;
$R_5$ is H, straight chain saturated alkyl, straight chain unsaturated alkyl, branched chain saturated alkyl, or branched chain unsaturated alkyl;
$R_6$ is O, NH, or S;
$R_7$ is H, straight chain saturated alkyl, straight chain unsaturated alkyl, acyl or aryl;
$R_8$ is H;
and
Z is H.

6. A composition comprising the compound of claim 1 and a pharmaceutically acceptable excipient.

7. A composition comprising the compound of claim 2 and a pharmaceutically acceptable excipient.

8. A composition comprising the compound of claim 3 and a pharmaceutically acceptable excipient.

9. A composition comprising the compound of claim 4 and a pharmaceutically acceptable excipient.

10. A process for preparing a diazonamide compound comprising the steps of:
a) A, E and F-ring assembly according to the scheme

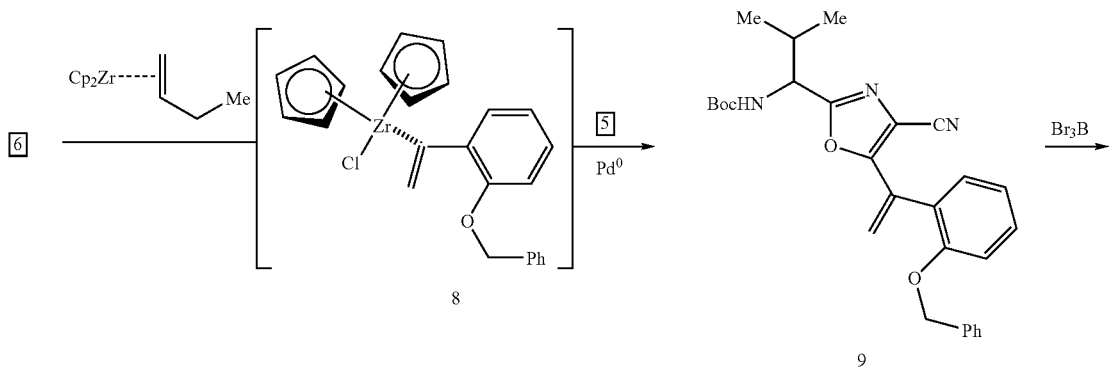

31
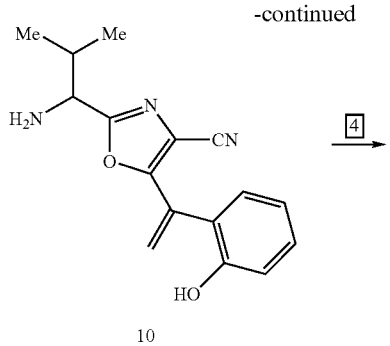
10
-continued
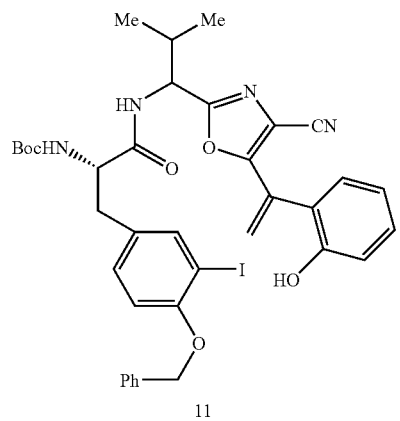
11
wherein
4 is
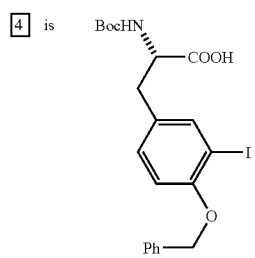
5 is
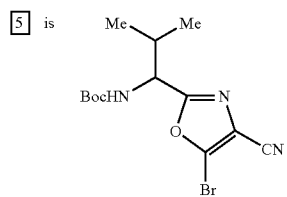
6 is
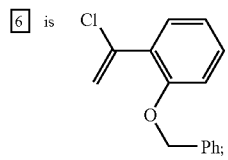
b) Heck endocyclization;
c) ring-contracting pinacol rearrangement; and
d) internal indole arylation via photo-induced electron transfer cyclization, wherein A, E and F-ring nomenclature is shown in the following diazonamide structure:
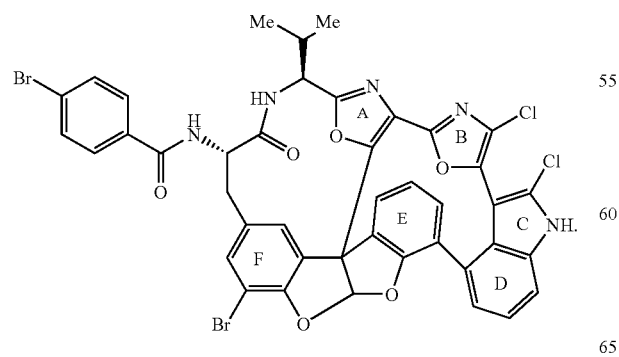
* * * * *